United States Patent [19]
Burke

[11] Patent Number: 5,552,156
[45] Date of Patent: Sep. 3, 1996

[54] LIPOSOMAL AND MICELLULAR STABILIZATION OF CAMPTOTHECIN DRUGS

[75] Inventor: Thomas G. Burke, Columbus, Ohio

[73] Assignee: Ohio State University, Columbus, Ohio

[21] Appl. No.: 407,989

[22] Filed: Mar. 22, 1995

Related U.S. Application Data

[63] Continuation of Ser. No. 965,933, Oct. 23, 1992, abandoned.

[51] Int. Cl.$^6$ .................................................. A61K 9/127
[52] U.S. Cl. ............................................................ 424/450
[58] Field of Search ............................................. 424/450

[56] References Cited

U.S. PATENT DOCUMENTS

| | | | |
|---|---|---|---|
| 4,812,312 | 3/1989 | Berestein | 424/450 |
| 5,145,684 | 9/1992 | Liversidge | 424/489 |

FOREIGN PATENT DOCUMENTS

| | | | |
|---|---|---|---|
| US94/10898 | 4/1995 | WIPO . | |

OTHER PUBLICATIONS

Szoka Ann. Rev. Biophys. Bioeng., 9, 467, 1980.

Ostro, Liposomes, p. 277, 1987.

"The Role of Liposome Composition on the Stabilization of Ancitabine," Satish K. Pejaver et al., The Ohio State University, 1987, pp. 2633–2649.

"Liposomal Stabilization of Camptothecin's Lactone Ring", Burke et al., Journal of American Chemical Society, 1992, p. 114.

"Liposomes for the Sustained Drug Release in Vivo", Blume et al., Biochimica et Biophysica Act, Elsevier Science Publishers, 1990, vol. 1029, pp. 91–97.

"Liposomes as Carriers of Antitumor Agents: Toward a Clinical Realty", R. Perez–Soler, Cancer Treatment Reviews, Academic Press Limited, 1989, vol. 16, pp. 67–82.

"Liposome Preparation and Size Characterization", by Woodle et al., Methods in Enzymology, Academic Press, Inc. 1989, vol. 171, pp. 193–217.

"Interactions of Liposomes with Mammalian Cells", Pagano et al., Ann. Rev. Biophys. Bioeng., Annual Reviews Inc., 1978, vol. 7, pp. 435–468.

"Liposomes", Lasic, Danilo, American Scientist, Jan.–Feb. 1992, vol. 80, pp. 20–31.

"Selective in Vivo Localization of Daunorubicin Small Unilamellar Vesicles in Solid Tumors", by Forssen et al., Cancer Research 52, pp. 3255–3261, Jun. 15, 1992.

"Influence of Vesicle Size, Lipid Composition, and Drug–to–Lipid Ratio on the Biological Activity of Liposomal Doxorubicin in Mice", Mayer et al., Cancer Research 49, Nov. 1, 1989, pp. 5922–5930.

"Microscopic Localization of Sterically Stabilized Liposomes in Colon Carcinoma–bearing Mice" Huang et al., Cancer Research 52, pp. 5135–5143, Oct. 1, 1992.

(List continued on next page.)

Primary Examiner—Gollamudi S. Kishore
Attorney, Agent, or Firm—Calfee Halter & Griswold

[57] ABSTRACT

The present invention provides water soluble, stable, highly pharmacologically active camptothecin drugs by solubilizing the camptothecin drugs in liposomes composed of lipids or in micelles composed of surfactants. The invention overcomes both the insolubility problems and instability problems of the drugs administered in their free form. The pH of the internal environment of the liposomes or micelles may be reduced pH which prevents hydrolysis of those camptothecin drugs which have lower affinity for the liposome or micelle membrane. Typically in the liposomes, the lactone ring of drug intercalates in between the lipid acyl chains, in a protected environment well removed from the aqueous interface. In this manner the lactone ring of the drug is stabilized and the biologically active form of camptothecin drugs are conserved.

17 Claims, 16 Drawing Sheets

OTHER PUBLICATIONS

"Tumoricidal Effects of Liposomes Containing Phosphatidylinositol or Phosphatidylcholine" Jett et al., Methods in Enzymology, vol. 141, pp. 459–466, 1987.

"Influence of Lipid Composition on the Antitumor Activity Exerted by Doxorubicin–containing Liposomes in a Rat Solid Tumor Model" Storm et al., Cancer Research 47, pp. 3366–3372, Jul. 1, 1987.

"Liposome formulations with Prolonged Circulation Time in Blood and Enhanced Uptake by Tumors" Gabizon et al., Proc. Natl. Acad. Sci. USA vol. 85, pp. 6949–6953, Sep. 1988.

"Mixed Micelles as a Proliposomal Lymphotropic Drug Carrier" Supersaxo et al., Pharmaceutical Research, vol. 8, No. 10, pp. 1286–1291, 1991.

"Small Liposomes are better than Large Liposomes for Specific Drug Delivery in Vitro" Machy et al., Biochimica et Biophysica Acta, 730, pp. 313–320, 1983.

"Stealth Liposomes: An Improved Sustained Release System for 1–β–D–Arabinofuranosylcytosine" Allen et al., Cancer Research 52, pp. 2431–2439, May 1, 1992.

"Sterically stabilized liposomes: Improvements in pharmacokinetics and antitumor therapeutic efficacy" Papahadjopoulos et al., Proc. Natl. Acad. Sci. USA 88, pp. 11460–11464, Dec. 1991.

"Enhancement of Murine Tumor Cell Sensitivity to Adriamycin by Presentation of the Drug in Phosphatidyl–choline–Phosphatidylserine Liposomes" Fan et al., Cancer Research 50, pp. 3619–3626, Jun. 15, 1990.

"Interaction of Positively–charged Liposomes with Blood: Implications for their application in vivo" Senior et al., Biochimica et Biophysica Act 1070, pp. 173–179, 1991.

"Effect of Liposome Composition and other Factors on the Targeting of Liposomes to Experimental Tumors: Biodistribution and Imaging Studies" Gabizon et al., Cancer Research 50, pp. 6371–6378, Oct. 1, 1990.

"Liposomes with prolonged circulation times: Factors affecting uptake by reticuloendothelial and other tissues" Allen et al., Biochimica et Biophysica Acta 981, pp. 27–35, 1989.

"Liposome delivery of Antisense Oligonucleotides: Adsorption and Efflux characteristics of Phosphorothioate Oligodeoxynucleotides" by Akhtar et al., Journal of Controlled Release 22 (1992) 47–56.

"Modulation of Doxorubicin Resistance by Valinomycin (NSC 122023) and Liposomal Valinomycin in Chinese Hamster Ovary Cells" Daoud et al., Cancer Research 49, pp. 2661–2667, May 15, 1989.

"Anti–Laminin Receptor Antibody Targeting of Liposomes with Encapsulated Doxorubicin to Human Breast Cancer Cells in Vitro" Rahman et al., Journal of National Cancer Institute 81, pp. 1794–1989, 1989.

"Phase I Clinical and Parmacological Study of Liposome–entrapped cis–Bis–neodecanoato–trans–R,R–1,2–diaminocylcohexane Platinum(II)" Perez–Soler et al., Cancer Research 50, pp. 4254–4259, 1990.

"Pharmacological, Toxicological and Therapeutic Evaluation in Mice of Doxorubicin Entrapped in Cardiolipin Liposomes" Rahman et al., Cancer Research 45, pp. 796–803, Feb. 1985.

"Method for Rapid Separation of Liposome–Associated Doxorubicin from Free Doxorubicin in Plasma" Thies et al., Analytical Biochemistry 188, pp. 65–71, 1990.

"Generation and Characterization of Iron– and Barium–loaded Liposomes" Chakrabarti et al., Biochimica et Biophysica Acta 1108, pp. 233–239, 1992.

"Augmentation of Antiproliferative Activity of Interferon Alfa Against Human Bladder Tumor Cell Lines by Encapsulation of Interferon Alfa Within Liposomes" Killion et al., Jounal of National Cancer Institute vol. 81, No. 18, pp. 1387–1392, Sep. 20, 1989.

Pharmaceutical Dosage Forms Disperse Systems edited by Lieberman, Herbert A., pp. 334–338 from Chapter 8 "Surfactants" (1988) Marcel Kekker Inc.

"Complete Inhibition of Growth followed by Death of Human Malignant Melanoma Cells in Vitro and Regression of Human Melanoma Xenografts in Immunodeficient Mice Induced by Captothecins" Pantazis et al., Cancer Research 52, pp. 3980–3987, Jul. 15, 1992.

"DNA Topoisomerase I–Targeted Chemotherapy of Human Colon Cancer in Xenografts" Giovanella et al., Science 246, pp. 1046–1048, Nov. 24, 1989.

"Complete Growth Inhibition of Human Cancer Xenografts in Nude Mice by Treatment with 20–(S)–Camptothecin" by Giovanella et al., Cancer Research 51, pp. 3052–3055, Jun. 1, 1991.

"Activity of Topotecan, a New Topoisomerase I Inhibitor, Against Human Tumor Colony–Forming Unites In Vitro" Burris et al., Journal of National Cancer Institute 84, No. 23, pp. 1816–1820, Dec. 2, 1992.

LIPOSOMAL AND MICELLULAR STABILIZATION OF CAMPTOTHECIN DRUGS

This is a continuation of application Ser. No. 07/965,933 filed on Oct. 23, 1992 now abandoned.

BACKGROUND OF THE INVENTION

Camptothecin, a plant alkaloid isolated from trees indigenous to China, and analogues thereof such as 9-aminocamptothecin, 10-hydroxycamptothecin, 10,11-methylenedioxycamptothecin, 9-nitro-10,11-methylenedioxycamptothecin, 9-chloro-10,11-methylenedioxycamptothecin, 9-amino-10,11-methylenedioxycamptothecin, 9-nitrocamptothecin, topotecan, and other analogues (collectively referred to herein as "camptothecin drugs") are presently under study worldwide in research laboratories and cancer clinics. In lab tests and in clinical trials, the camptothecin drugs have aroused considerable interest as a result their ability to halt the growth of a wide range of human tumors. For example, these drugs exhibit unprecedented high levels of antitumor activities against human colon cancer, Giovanella, et al. Science 246: 1046–1048 (Washington, D.C.) (1989). Camptothecin has also been shown to be effective against other experimental cancer types such as lung, breast, and malignant melanoma.

Camptothecin is thought to inhibit the proliferation of cancer cells by interfering with the breakage/reunion reaction of the enzyme topoisomerase I, a nuclear enzyme implicated in DNA replication and RNA transcription. The camptothecin stabilizes and forms a reversible enzyme-camptothecin-DNA ternary complex, designated the "cleavage complex". The formation of the cleavable complex specifically prevents the reunion step of the breakage/union cycle of the topoisomerase reaction.

However, the clinical use of the camptothecin drugs is limited by their chemical properties. First, the camptothecin drugs are insoluble in water which hinders the delivery of the drug to the cancer cells. Second, the camptothecin drugs are extremely susceptible to hydrolysis; in an aqueous environment such as blood plasma, the half life is about 16 to 29 minutes. The camptothecin drugs each contain a substituted quinoline nucleus (rings A-C) and, at the opposite end an α-hydroxy lactone ring which is very unstable in aqueous environments. In blood plasma the ring is quickly opened to create the carboxylate form of the drug, which is poorly accumulated by cancer cells. Once internalized by the cancer cells, the carboxylate form exhibits no activity against its molecular target, topoisomersase I. Thus, The hydrolysed product is ineffective at treating cancer. Moreover, the hydrolysed product appears to be more toxic to healthy tissue than the camptothecin drugs.

Attempts have been made to improve the clinical utility of the camptothecin drugs by modifying the chemical structure of the camptothecin drugs. Specifically, attempts have been made to increase the water solubility of the camptothecin drugs by introducing additional hydroxyl groups on the camptothecin drug molecules. While such modifications have improved the water solubility of the camptothecin drugs, they have had the concomitant effect of decreasing the pharmacological activity of the drugs.

It is desirable to have camptothecin drugs that are stable, water soluble, relatively non toxic, that still maintain antitumor activity.

SUMMARY OF THE INVENTION

This invention overcomes both the insolubility problems and instability problems of the camptothecin drugs administered in their free form. It has been discovered that the lactone ring of the camptothecin drugs is stabilized in the membranes of vesicles. The present invention provides water soluble, stable, highly pharmacologically active camptothecin drugs by stabilizing the camptothecin drugs in vesicles such as liposomes and micelles. Typically, the camptothecin drugs bind the lipid bilayer membrane of the liposome and the surfactant monolayer membrane of the micelles with high affinity. The liposome-bound drug is protected from hydrolysis, thus preserving the antitumor activity of the drug. The liposome is comprised of lipids such as, for example phospholipids or cholesterol. For the camptothecin drugs which have a lower affinity for the liposome membrane and thus disassociate from the liposomal membrane to reside in the interior of liposome, the pH of the internal environment of the liposomes is reduced thereby preventing hydrolysis of such camptothecin drugs. Camptothecin drugs are also stabilized by association with micelles comprised of surfactants such as sodium dodecylsulfate (SDS), octylphenolpolyoxyethylene glycol and sorbitan mono-oleate.

DETAILED DESCRIPTION OF THE INVENTION

Figure 1A:
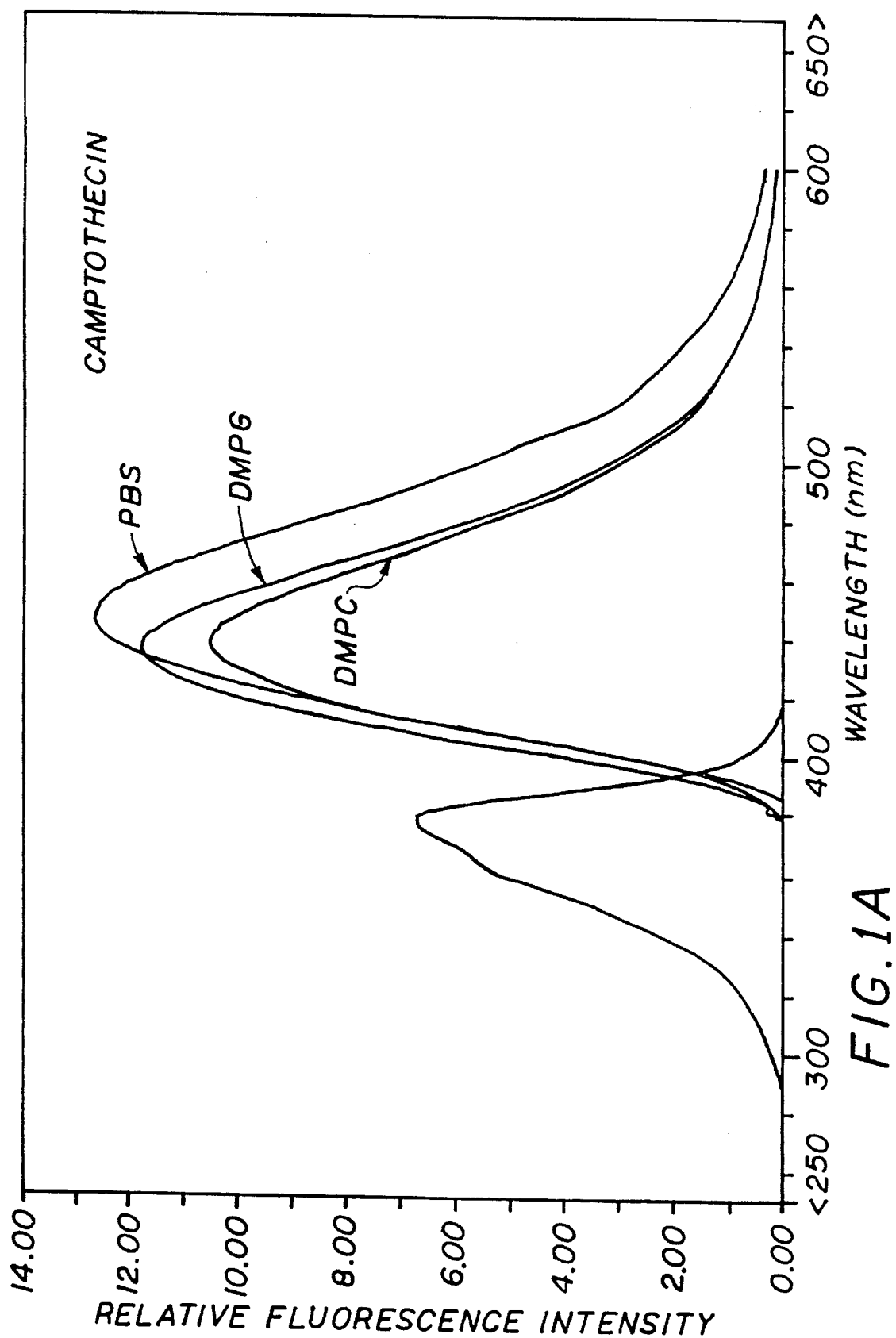
FIG. 1a. is the fluorescence excitation and emission spectra of camptothecin free in PBS and camptothecin associated with DMPG liposomes and DMPC liposomes.

The present invention provides water soluble, stable, highly pharmacologically active camptothecin drugs by solubilizing the camptothecin drugs in receptacles. The receptacles are liposomes, comprised of lipids such as cholesterol, or phospholipids, or micelles comprised of surfactant such as, for example, sodium dodecylsulfate, octylphenolpolyoxyethylene glycol, or sorbitan mono-oleate. Typically, the camptothecin drugs bind the lipid bilayer the membrane of liposome with high affinity. The liposome bound camptothecin drug intercalates between the acyl chains of the lipid. The lactone ring of the camptothecin membrane-bound drug is thereby removed from the aqueous environment inside and outside of the liposome and thus protected from hydrolysis. Since the liposome-bound drug is protected from hydrolysis, the antitumor activity of the drug is preserved. For the camptothecin drugs, such as topotecan, which have a lower affinity for the liposome membrane and thus disassociate from the liposome membrane to reside in the interior of liposome, the pH of the interior of the liposomes may be reduced thereby preventing hydrolysis of such camptothecin drugs.

Unilamellar liposomes, also referred to as single lamellar vesicles, are spherical vesicles comprised of one lipid bilayer membrane which defines a closed compartment. The bilayer membrane is composed of two layers of lipids; an inner layer and an outer layer. The outer layer of lipid molecules are oriented with their hydrophilic head portions toward the external aqueous environment and their hydrophobic tails pointed downward toward interior of the liposome. The inner layer of lipid lays directly beneath the outer layer; the lipids are oriented with their heads facing the aqueous interior of the liposome and their tails toward the tails of outer layer of lipid.

Multilamellar liposomes, also referred to as multilamellar vesicles are composed of more than one lipid bilayer membrane, which membranes define more than one closed compartment. The membranes are concentrically arranged so that the different membranes are separated by compartments much like an onion skin.

As used herein the terms "camptothecin drugs are associated with liposomes" means either that some or all of the camptothecin drug is located in one or more of the compartments of the liposome or the camptothecin drug is bound to the membrane of the liposome, to provide a liposome comprising a lipid bilayer membrane and a camptothecin drug. As used herein, the phrase "bound to lipid membrane" means that at least the lactone ring of some or all of the camptothecin drug binds to the lipid membrane of the liposome where the liposome contains more than 1 bilayer membrane the camptothecin drug is bound to at least 1 membrane. Those camptothecin drugs that have a high affinity for such membrane tend to remain bound to the membrane. Those camptothecin drugs with a low affinity for the liposome membrane, such as topotecan, will at least partially disassociate from the liposome membrane and reside in the liposome compartment.

Micelles are spherical receptacles comprised of a single, monolayer membrane which defines a closed compartment. The micelle membrane is comprised of surfactant molecules oriented so that the hydrocarbon tails are oriented toward the compartment and the polar head portions are oriented toward the external aqueous environment. The camptothecin drugs, when associated with micelles, are either: in the compartment; or bound to the micelle membrane; or bound to the outside surface of the micelle.

Liposomes have been used successfully to administer medications to cancer patients, and have been shown to be useful clinically in the delivery of anticancer drugs such as doxorubicin, daunorubicin, and cisplatinum complexes. Forssen, et al., *Cancer Res.* 1992, 52: 3255–3261; Perez-Soler, et al. *Cancer Res.* 1990, 50: 4260–4266; and, Khokhar, et al. *J. Med. Chem.* 1991, 34: 325–329, and references cited therein.

Similarly, micelles have also been used to deliver medications to patients, (Brodin et al., *Acta Pharm. Suec.* 19 267–284 (1982)) and micelles have been used as drug carriers and for targeted drug delivery, (D. D. Lasic, *Nature* 335: 279–280 (1992); and, Supersaxo et al., *Pharm. Res.* 8: 1286–1291 (1991)), including cancer medications, (Fung et al., *Biomater. Artif. Cells. Artif. Organs* 16: 439 et. seq. (1988); and Yokoyama et al., *Cancer Res.* 51: 3229–3236 (1991)).

The liposomes and micelles containing camptothecin drugs are administered to the cancer patient, typically intravenously. The liposomes and micelles are carried by the circulatory system to the cancer cells where the membrane of the vesicle fuses to the membrane of the cancer cell thereby releasing the camptothecin drug to the cancer cell, or where the liposomes and micelles remain adjacent to the cancer cells and the camptothecin drugs diffuses from the liposomes and micelles to be taken up by the cancer cells.

The Camptothecin Drugs

Any of the camptothecin drugs which exhibit anti-tumor activity are suitable for use in the present invention. The camptothecin drugs have a similar structure shown below:

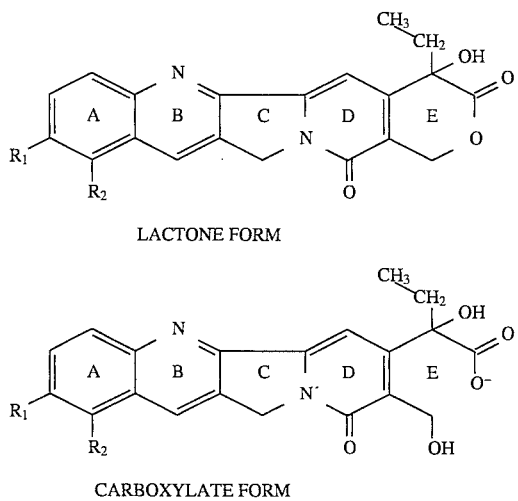

Several examples of Camptothecin Drugs are provided in Table I.

TABLE I

| CAMPTOTHECIN DRUG | $R_1$ | $R_2$ |
|---|---|---|
| CAMPTOTHECIN | H | H |
| 9-AMINOCAMPTOTHECIN | H | $NH_2$ |
| 9-NITROCAMPTOTHECIN | H | $NO_2$ |
| 10-HYDROXYCAMPTOTHECIN | OH | H |
| TOPOTECAN | OH | $CH_2NH(CH_3)_2$ |

Other camptothecin drugs have the following structure:

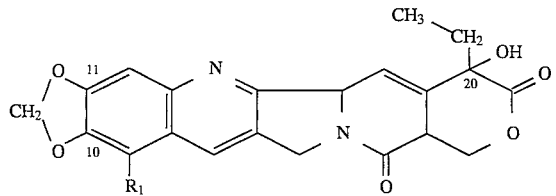

Where R1 is Cl, the drug is 9-chloro-10,11-methylenedioxycamptothecin; where R1 is $NH_2$, the drug is 9-amino-10,11-methylenedioxycamptothecin; where R1 is H, the drug is 10,11-methylenedioxycamptothecin.

Camptothecin, camptothecin carboxylate carboxylate sodium salt, 10-hydroxycamptothecin, 10,11-methylenedioxycamptothecin, 9-aminocamptothecin and topotecan were obtained from the National Cancer Institute, Division of Cancer Treatment. Samples of 9-chloro-10,11-methylendioxycamptothecin (CMC), 9-amino-10,11-methylenedioxycamptothecin (AMC) and 9-nitrocamptothecin were obtained for the laboratory of Drs. Monroe Wall and Mansukh Wani of the Research Triangle Institute, Research Triangle, N.C. Stock solutions of the camptothecin drugs were prepared in dimethylsulfoxide A.C.S. spectrophotometric grade, from Aldrich Chemical, Milwaukee, Wis. at a concentration of $2 \times 10^{-3}$ M and stored in dark at 4° C. The concentration of the camptothecin drug associated with the liposomes or micelles may be adjusted as desired depending on the dose selected for the treatment of the patient. As long as the ratio or the concentration of the camptothecin to the concentration of lipid provides for an excess of lipid, the camptothecin drug will be stabilized by the liposome. Similarly, as long as the surfactant concentration provides for an excess of surfactant, the camptothecin drug will be stabilized by the micelles.

In addition to the camptothecin drugs, the liposomes and micelles of the present invention will stabilize other drugs which contain a lactone ring, such as for example bryostatin and its analogues, and Rhizoxin.

The Lipid

Any lipid or mixture of lipids which forms liposomes is suitable for use in the present invention. Phosphatidylcholines, including, for example, L-α-dimyristoylphosphatidylcholine (DMPC), L-α-dipalmitoylphosphatidylcholine (DPPC) and L-α-distearoylphosphatidylcholine (DSPC) are suitable. Also, phosphatidylglycerols, including, for example, L-α-dimyristoylphosphatidylglycerol (DMPG) are suitable. The DMPC and DMPG are both fluid phase at 37° C., while DSPC is solid phase at 37° C. Since the presence of negatively charged lipid in the liposome membrane causes the liposomes to repel each other, small amounts, such as, for example about 10%, of an negatively charged lipid, such as distearolphosphotidylglycerol (DSPG), may be incorporated into the DSPC liposomes. Other suitable phospholipids include: phosphatidyl-ethanolamines, phosphatidylinositols, and phosphatidic acids containing lauric, myristic, palmitic, palmitoleic, stearic, oleic, linoleic, arachidonic, behenic and lignoceric acid. Another suitable lipid includes cholesterol.

Also, liposomes may be coated with polyethyleneglycol or $GM_1$ protein which assists the particles in avoiding the reticuloendothelial system.

DSPC, since it is solid phase at 37° C., (the average temperature of humans), limits the diffusion of the camptothecin drug from the liposome and thus can be employed to time release the camptothecin drugs.

The DMPG, DPPC, and DSPC used herein were obtained from Avanti Polar Lipids, Alabaster, Ala. and were used without further purification. All other chemicals were reagent grade and were used without further purification.

The Surfactant

Any surfactant or mixtures thereof, which forms micelles is suitable for use in the present invention. Suitable surfactants include sodium dodecylsulfate (SDS) available from Kodak, Rochester, N.Y., octylphenolpolyoxyethylene glycol, available under the trade name "Triton X-100" from Aldrich Chemical Co., Milwaukee, Wis., and sorbitan mono-oleate, available under the trade name "Polysorbate 80" and "Tween 80" from Sigma Chemical Co. Other suitable surfactants include, for example, deoxycholic acid sodium salt, cholic acid sodium salt, and polyoxyethylene-10-cetylether, available under the trade name "BRIJ-56"; these surfactants are available from Sigma Chemical Co.

In addition, micelles may be composed of lipid, such as phospholipid, and mixtures of lipids. Also micelles may be composed of both lipid and surfactant.

LIPOSOME & MICELLE PREPARATION

Liposome Preparation

Liposome suspensions were prepared the day of an experiment by the method of Burke and Tritton Biochemistry 24: 1768–1776 (1985). Unless otherwise noted, the

7 liposomes were small unilamellar vesicles (SUV), rather than multilamellar vesicles (MLV). However, both SUVs and MLVs are within the scope of the invention. While MLVs have the advantage of limiting the rate of diffusion of the associated camptothecin drug, they have the disadvantage of being more easily scavenged by macrophages than the SUVs. Stock lipid suspensions containing 200 mg/mL lipid in phosphate-buffered saline (PBS) containing 8 mM $Na_2HPO_4$, 1 mM $KH_2PO_4$, 137 mM NaCl, and 3 mM KCl having a pH of 7.4 were prepared by vortex mixing for 5–10 min above the gel-liquid-crystalline phase transition temperature $T_M$ of the lipid. The lipid suspensions were then sonicated using a bath-type sonicator from Laboratory Supplies Co., Hicksville, N.Y., for 3–4 hours until they became optically clear. A decrease in pH from 7.4 to 6.8 was observed for the SUV preparations of DMPG; therefore, the pH of these SUV suspensions was adjusted to 7.4 using small quantities of 2.5M NaOH in PBS and sonicated again. Each type of liposome suspension was annealed for 30 minutes at 37° C.

EXAMPLE 1

Small unilamellar liposomes composed of dimyristoyl phosphatidylcholine were prepared as follows. Dry lipid powder DMPC from Avanti Polar Lipids was weighed out and suspended at a concentration of 0.29M lipid in PBS buffer at a pH of 7.4. This suspension was heated to approximately 40° C. a temperature above the phase transition temperature ($T_m$) of the lipid and aggressively mixed by vortex while maintaining the temperature at about 40° C. which produced multilamellar vesicles. These MLVs were then sonicated in a glass tube in a bath-type sonicator from Laboratory Supplies Co., Hicksville, N.Y., for 1 to 4 hours or until the sample became optically clear. The optical clarity indicates that particle size has been reduced to the 350–600 A° range.

EXAMPLE 2

Small unilamellar liposomes composed of dimyristoyl phosphatidylglycerol (DMPG) were prepared as in Example 1, using DMPG rather than DMPC. However, after the sonication, a decrease in pH from 7.4 to 6.8 was observed for the SUV preparations of DMPG; therefore, the pH of these suspensions was adjusted to 7.4 using small quantities of 2.5M NaOH in PBS. Following addition of the NaOH, the sample was resonicated for 1 to 2 hours.

EXAMPLE 3

Small unilamellar liposomes composed of distearoyl phosphatidylcholine (DSPC) were prepared as in Example 1, using DSPC rather than DMPG. However, the sonication was performed for more than 5 hours.

Stock solutions were made of the following camptothecin drugs: camptothecin; 10-hydroxycamptothecin; topotecan; 9-aminocamptothecin; 9-nitrocamptothecin; 10,11-methylenedioxycamptothecin; 9-amino-10,11-methylenedioxycamptothecin; and 9-chloro-10,11-methylenedioxycamptothecin, at a concentration of $2 \times 10^{-3}$M in PBS. Aliquots of the stock solutions were added to the SUV suspensions of Examples 1–3 to provide final drug concentrations of 1 µM, 2 µM and 2 mM.

Specifically: camptothecin; 10-hydroxycamptothecin; topotecan; 9- aminocamptothecin; 10,11-methylenedioxycamptothecin; 9-amino-10,11-methylenedioxycamptothecin; 9-chloro-10,11-methylenedioxycamptothecin were added to the DMPC liposomes of example 1, at a final drug concentration of 1 µM. Camptothecin; 10-hydroxycamptothecin; topotecan; 9-aminocamptothecin; 10,11-methylenedioxycamptothecin; were added to the DMPC liposomes of example 1 at a final drug concentration of 2 µM. Camptothecin; 10-hydroxycamptothecin; topotecan; 10,11-methylenedioxycamptothecin; 9-chloro-10,11-methylenedioxycamptothecin; were added to the DMPG liposomes of example 2, at a final drug concentration of 1 µM. Camptothecin; 10-hydroxycamptothecin; topotecan; 9-aminocamptothecin; 10,11-methylenedioxycamptothecin; 9-chloro-10,11-methylenedioxycamptothecin; were added to the DMPG liposomes of example 2, at a final drug concentration of 2 µM. Camptothecin and topotecan were added to the DSPC liposomes of example 3, at a final drug concentration of 1 µM. Camptothecin was added to the DMPC liposomes of example 1 and Example 5, at a final drug concentration of 2 mM.

EXAMPLE 4

Multilamellar vesicles composed of DMPC were prepared by weighing out $5.8 \times 10^{-4}$ mol. of DMPC and dissolving the DMPC in 1 ml of chloroform. Then $4 \times 10^{-6}$ mol. of CMC was added to the DMPC chloroform solution and mixed thoroughly, to provide a lipid concentration of 0.29M and a total drug concentration of 2 µM. The chloroform was then removed by using a stream of nitrogen and heat to produce a DMPC film. The DMPC films were then dried overnight in a vacuum desiccator to remove any trace of residual chloroform. Next, 2 ml of PBS was added to the DMPC films and the films were heated to 35° C. and agitated for 5 minutes.

EXAMPLE 5

DMPC MLVs were prepared as in Example 4, except that camptothecin was used instead of CMC.

EXAMPLE 6

DMPC MLVs were prepared as in Example 4, except that 10,11-methylenedioxycamptothecin was used instead of CMC.

EXAMPLE 7

DSPC multilamellar vesicles having an internal pH of 5 were prepared by weighing out $1.4 \times 10^{-4}$ mol. of DSPC and dissolving it in 2 ml of chloroform. Next, $4 \times 10^{-7}$ mol. of CMC was weighed out and added to the DSPC chloroform solution, to provide a total CMC concentration of 0.2 mM, and a total lipid concentration of 0.07. The solution was mixed and the chloroform was removed as described in Example 4, to provide a film. Next, 2 ml PBS buffer at pH 5 was added to the film, the film was heated to approximately 60° C. and vortexed at this temperature. The sample was then cooled to 37° C. which is below the $T_m$ of the DSPC, so that diffusion of camptothecin drugs out of the liposome is slowed. The pH outside the liposomes was adjusted to pH 7.4, and the sample diluted 100 fold to provide a total lipid concentration of 0.0007M.

MICELLES

EXAMPLE 8

SDS micelles were prepared from the surfactant sodium dodecylsulfate (SDS) from Kodak, Rochester, N.Y., by preparing a solution of SDS at a concentration of 200 mg/ml in PBS at pH 7.4. At this concentration, the surfactant is well above its critical micelle concentration value and spontaneously assembles into micelles, to provide a suspension of micelles.

EXAMPLE 9

Octylphenolpolyoxyethylene micelles were prepared as in Example 8 except that Triton X-100 reduced, from Aldrich Chemical Co., Milwaukee, Wis., was used instead of SDS.

EXAMPLE 10

Sorbitan mono-oleate micelles were prepared as in Example 8, except that Tween 80 from Sigma Chemical, St. Louis, Mo., was used instead of SDS.

Aliquots of the 10,11-methylenedioxycamptothecin stock solution were added to the micelle suspensions of Examples 8–10 to provide a final drug concentration of 1 µM. Aliquots of the 9-chloro-10,11-methylenedioxycamptothecin stock solution were added to the micelle suspensions of example 10 to provide a final drug concentration of 1 um.
Characterization of Camptothecin Drugs Associated with Liposomes The camptothecin drugs are intrinsically intensely fluorescent. Fluorescence is associated with the extended conjugation of the quinoline ring system. The liposomes of Examples 1–7 were characterized for the presence of the camptothecin drugs, using excitation and emission spectrography, and fluorescence anisotropy.
Fluorescence Instrumentation Steady-state fluorescence measurements were obtained on a SLM Model 4800C. spectrofluorometer with a thermostated cuvette compartment. This instrument was interfaced with an IBM PS/2 model 55 SX computer. Excitation and emission spectra were recorded with an excitation resolution of 8 nm and an emission resolution of 4 nm. In all cases spectra were corrected for background fluorescence and scatter from unlabeled lipids or from solvents by subtraction of the spectrum of a blank. Steady-state fluorescence intensity measurements were made in the absence of polarizer. Steady-state anisotropy (a) measurements were determined with the instrument in the "T-format" for simultaneous measurement of two polarized intensities. The alignment of polarizers were checked routinely using a dilute suspension of 0.25 µm polystyrene microspheres from Polysciences, Inc, Warrington, Pa., in water; anisotropy values of >0.99 were obtained. The anisotropy was calculated from $a=(I_{vv}-GI_{VH})/(I_{vv}+GI_{VH})$, where $G-I_{VH}/I_{HH}$ and the subscripts refer to vertical and horizontal orientations of the excitation and emission polarizers, respectively.

Anisotropy measurements for camptothecin, camptothecin carboxylate sodium salt, and 10,11-methylenedioxycamptothecin were conducted using exciting light of 370 nm and 420 nm long wave pass filters on each emission channel in order to isolate the fluorescence signal from background scatter and signal. For topotecan a 400 nm excitation wavelength and a 500 nm emission filter were used and for 9-aminocamptothecin a 375 nm excitation and a wavelength 420 nm emission filter were used. For AMC and CMC, a 370 nm excitation wavelength and a 400 nm emission filter were used. For 10-hydroxycamptothecin 375 nm excitation wavelength 500 nm emission filter was used. Emission filters were obtained from Oriel Corp. Stamford, Conn. The combination of exciting light and emission filters allows one to adequately separate the fluorescence from the background signal. The contribution of background fluorescence, together with scattered light, was typically less than 1% of the total intensity. Since the lactone ring of the camptothecin drug undergoes hydrolysis in aqueous medium, all measurements were completed within the shortest possible time, less than 1 minute after mixing the drug stock solution with PBS or the liposomes. In each case, analysis was initiated immediately after mixing the drug stock solution with PBS or with the liposomes. All measurements were performed at 37° C. unless otherwise noted.
Excitation & Emission Spectra FIG. 1A shows the excitation and emission spectra of camptothecin free in solution and camptothecin that is bound to liposomes composed of (DMPG) and to DMPC. The relative fluorescence intensity of $1\times10^{-6}$M of camptothecin free in PBS buffer at 37° C. is shown. The emission spectra of the camptothecin was recorded using exciting light of 370 nm. Where camptothecin binds to DMPG liposomes, the emission intensity decreases and the $\lambda_{max}$ of the camptothecin emission spectrum exhibits a shift to a lower wavelength, that is "blue shifts," about 16 nm relative to the emission spectra of free camptothecin. The shift in the emission spectrum demonstrates that the camptothecin drug binds to and is solubilized in the membrane of the liposome. Specifically, this shift indicates that the camptothecin chromophore penetrates into the acyl chain region of the liposome membrane. As shown in FIG. 1A, a spectral shift of about 5 nm was observed for camptothecin associated with DMPC liposomes, indicating the camptothecin drug was soluble in the DMPC liposome membrane, as well.

Figure 1B:
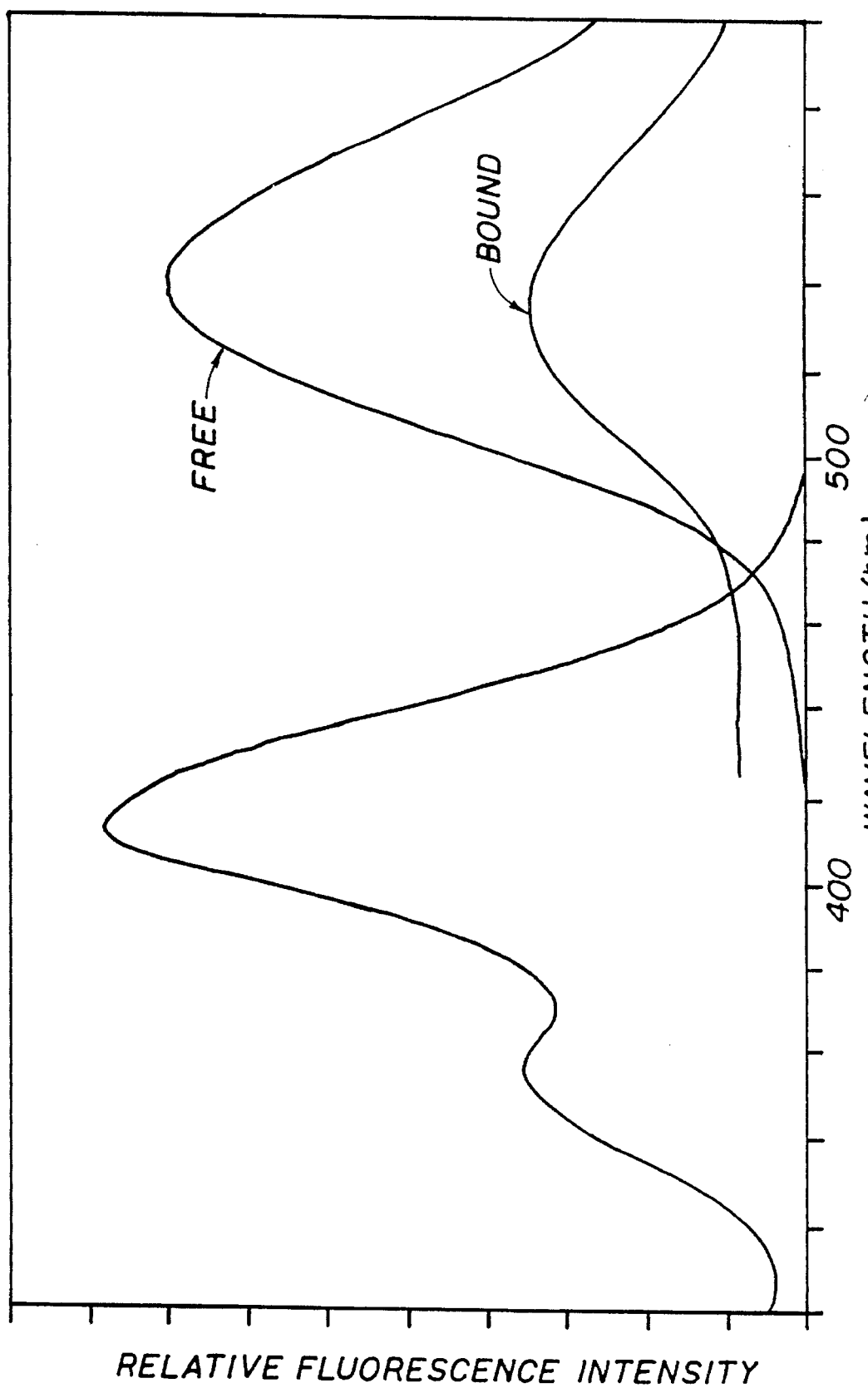
FIG. 1b. is the fluorescence excitation and emission spectra of free topotecan and topotecan associated with DMPG liposomes.

FIG. 1B shows the fluorescence excitation and emission spectra of 1 µM topotecan free in PBS and for topotecan associated with DMPG liposomes. An exciting light of 390 nm was used to record the emission spectra of topotecan. A decrease in the emission intensity is observed for topotecan associated with the DMPG liposome. Only a slight shifting in the emission spectrum of topotecan occurs in topotecan associated with DMPG liposomes, which indicates that topotecan does not strongly bind to the DMPG membrane of the liposome. Drug association with DMPC liposomes was also accompanied by blue shifting of the drug's emission spectrum, and a reduction in fluorescence intensity, indicating that the drug penetrated into the liposome membrane.

Since blue shifting of a fluorophore upon membrane binding is thought to involve relocation of the chromophore to a region area of lower dielectric constant, such as the acyl chain region of the membrane, the spectral data suggests that camptothecin penetrates more deeply into DMPG membrane relative to the positively charged topotecan.

Table II summarizes the fluorescence spectral parameters for camptothecin, topotecan and seven other camptothecin drugs both free in solution and bound to either DMPC or DMPG liposomes.

TABLE II

Fluorescence Spectral Parameters for Camptothecin Drugs Free in Solution and Bound to DMPC and DMPG Liposomes

| Compound | pH | $\lambda MX$ Excitation (nm) | PBS | DMPC | DMPG | Relative Fluorescence |
|---|---|---|---|---|---|---|
| camptothecin | 7.4 | 366 | 438 | 433 | 422 | 1 |
| camptothecin carboxylate[1] | 7.4 | 377 | 443 | 437 | 435 | 1 |
| 10-hydroxycamptothecin | 7.4 | 392 | 561 | 558 | 550 | 0.5 |
| topotecan | 7.4 | 410 | 537 | 538 | 533 | 1 |
| 9-aminocamptothecin | 7.4 | 381 | 439 | 442 | 436 | 0.001 |
| 9-aminocamptothecin | 3.0 | 381 | 464 | 477 | — | 0.001 |
| 9-nitrocamptothecin | 7.4 | 378 | 456 | — | — | 0.001 |
| 10,11-methylenedioxy-camptothecin | 7.4 | 395 | 410 | 408 | 408 | 1 |
| 9-amino-10,11-methylene-dioxycamptothecin | 7.4 | 404 | 550 | — | — | 0.001 |
| 9-amino-10,11-methylene-dioxycamptothecin | 1.5 | 373 | 430 | — | — | 0.06 |
| 9-chloro-10,11-methylene-dioxycamptothecin | 7.4 | 394[3] | 410 | — | 417 | 1 |

All spectra were recorded using camptothecin drug concentrations of 2 μM. The DMPC and DMPG concentrations were 0.29 M. Experiments were conducted in PBS buffer at 37° C.
[1]Camptothecin carboxylate sodium salt Table II shows the excitation and emission $\lambda_{MAX}$ for camptothecin drugs free in solution and bound to either DMPC liposome membrane or DMPG liposome membranes. Also found in Table II is a relative index of the emission intensity levels from these camptothecin drugs in PBS at their respective excitation and emission $\lambda_{MAX}$.

The camptothecin, topotecan, camptothecin carboxylate sodium salt, 10-hydroxycamptothecin, 10,11-methylenedioxycamptothecin and CMC all exhibit a strong fluorescence emission while free in PBS at pH 7.4. In contrast, 9-aminocamptothecin and 9-nitrocamptothecin do not; instead, they exhibit a 1000-fold reduction in emission intensity levels at pH 7.4 relative to camptothecin.

Figure 2:
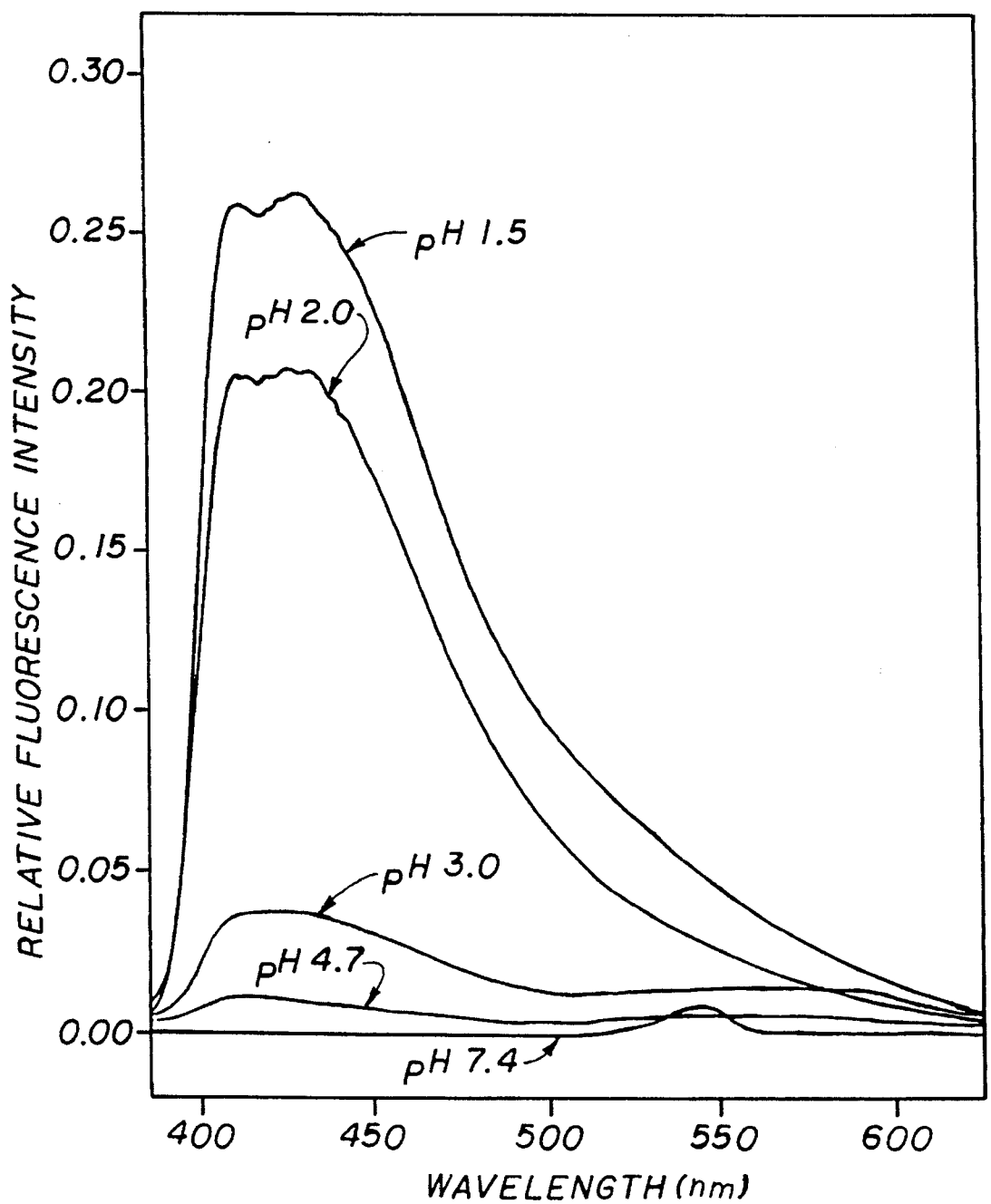
FIG. 2. is the fluorescence emission spectrum of free 9-amino-10,11-methylenedioxycamptothecin, at various pH values.
Figure 3A:
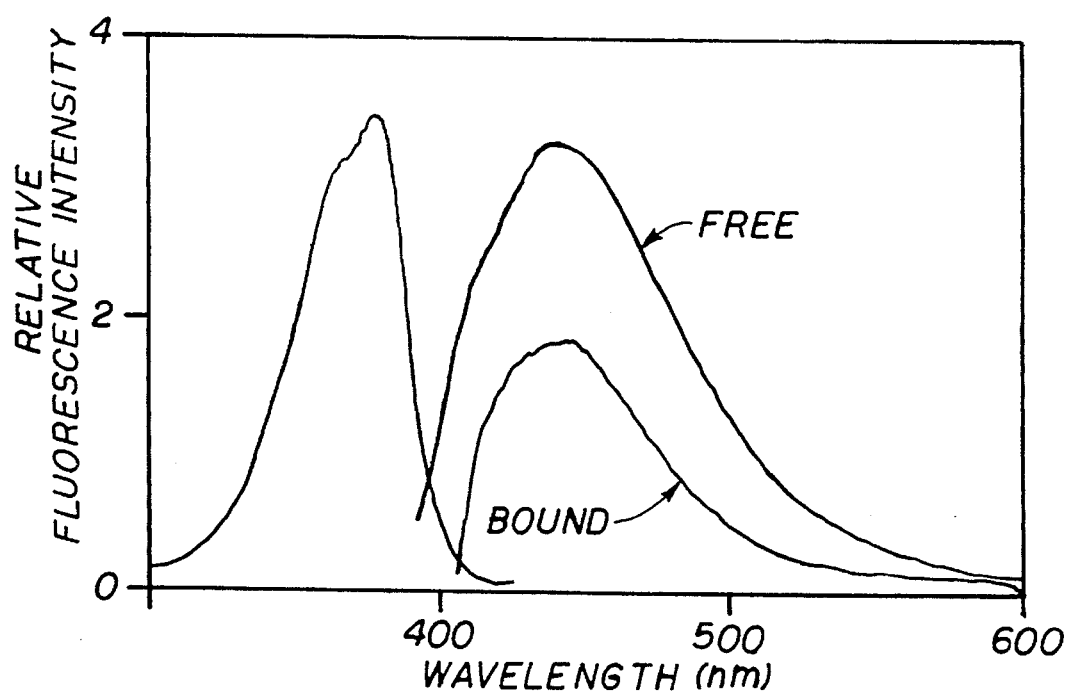
FIG. 3a. is the fluorescence excitation and emission spectra of 9-aminocamptothecin at pH 7.4 free in solution and associated with to DMPC liposomes.
Figure 3B:
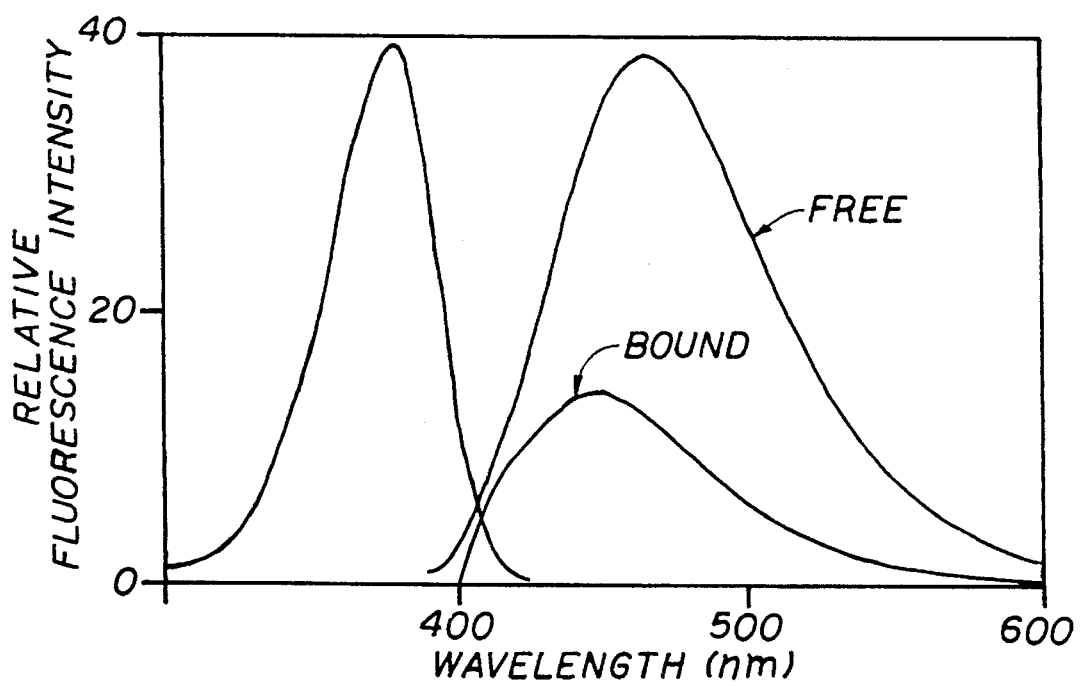
FIG. 3b. is the fluorescence excitation and emission spectra of 9-aminocamptothecin at pH 3.0 free in solution and bound to DMPC liposomes.

A 9-amino substitution of camptothecin results in very pH-sensitive emission spectra. FIG. 2 is the emission for 2 μM 9-amino-10,11-methylenedioxycamptothecin recorded at several different pH values using a excitation wave length of 370 nm. At pH 7.4 the 9-amino-10,11-methylenedioxycamptothecin displays a very weak fluorescence with an emission maxima observed at 550 nm. As the pH is decreased, the emission maxima shifts about 120 nm to a value of 430 nm, and the fluorescence quantum yield increases. A similar dependence on pH was observed in the fluorescence emission intensity of the 9-aminocamptothecin. FIG. 3A shows spectra for 1 μM 9-aminocamptothecin free in PBS solution at pH 7.4 while FIG. 3B shows the spectra for the drug free in PBS at pH 3.0. The fluorescence intensity scale in FIG. 3B is ten times greater than FIG. 3A. Thus, the apparent protonation of the 9-amino group results in strong increase in the fluorescence quantum yield. However, in contrast with the blue shifting of the emission spectrum of the 9-amino-10,11-methylenedioxycamptothecin upon protonation, the spectrum of 9-aminocamptothecin in PBS red shifts about 25 nm upon protonation.

Table II also shows that substitution of a hydroxy group into camptothecin at the 10 position as in, for example, 10-hydroxycamptothecin and topotecan, red shifts the fluorescence the emission maxima of camptothecin.

FIGS. 3A and 3B also demonstrate that the association of the 9-aminocamptothecin with DMPC liposomes, both at pH 7.4 and at pH 3.0, modulate the spectral characteristics of 9-aminocamptothecin. FIG. 3A is the emission spectra of 9-aminocamptothecin both free and associated with liposomes at a pH of 7.4, while FIG. 3B is the emission spectra of 9-aminocamptothecin both free associated with liposomes at a pH of 3.0. Both FIG. 3A and 3B show a reduction in emission intensity upon association of the 9-aminocamptothecin with the liposome membrane; at pH 7.4 there is a slight red shifting of the spectrum. The $\lambda_{MAX}$ value changes from 439 nm for 9-aminocamptothecin free in PBS to 442 nm for 9-aminocamptothecin associated with DMPC liposomes. At pH 3.0 a spectral shift of 13 nm occurs, but it is towards the blue region of the spectrum.

Thus, the spectral changes of the various camptothecin drugs establish that when associated with the liposomes, the camptothecin drugs bind to the lipid membrane of the liposome.

Equilibrium Association Constants of Camptothecin Drugs for Liposomes

While the spectral changes provide qualitative evidence that the camptothecin drugs bind the liposome membranes, fluorescence anisotropy titration, offers the most sensitive means for quantitatively assessing the extent of the binding. The fluorescence anisotropy titration was performed according to the method of Burke and Tritton, Biochemistry 24: 1768–1776 (1985).

A steady-state fluorescence anisotropy (a) measurement is related to the rotational rate of the fluorescent molecule through the Perrin Equation:

$$a_0/a = 1 + (T/\phi) \qquad \text{(Equation 1)}$$

where $a_0$ is the limiting fluorescence anisotropy value, that is, the anisotropy value in the absence of depolarizing rotations, T is the excited-state lifetime, and $\phi$ is the rotational correlative time of the fluorophore. According to Equation 1, changes in either the T or $\phi$ values of a fluorescent compound can modulate its steady-state anisotropy.

The excited state-lifetime values of camptothecin free in solution was measured in PBS, glycerol, and methanol at 37° C. The lifetime values are 4.7 ns, 3.8 ns, and 3.5 ns, respectively. The average excited state-lifetime value of camptothecin when bound to DMPC liposome membrane is 3.7 ns. The measurements indicate that the excited-state lifetime of camptothecin is relatively insensitive to changes in solvent environment or to changes due to relocation of camptothecin from an aqueous environment to the lipid liposome membrane. For such a compound whose T value remains relatively constant, the Perrin equation indicates that the relationship between a and φ values is straightforward: as the φ value of the fluorescent compound increases, whether due to an increase in solvent viscosity or enhanced associations with large macromolecular assemblies such as liposome, so does the steady-state anisotropy value.

Figure 5:
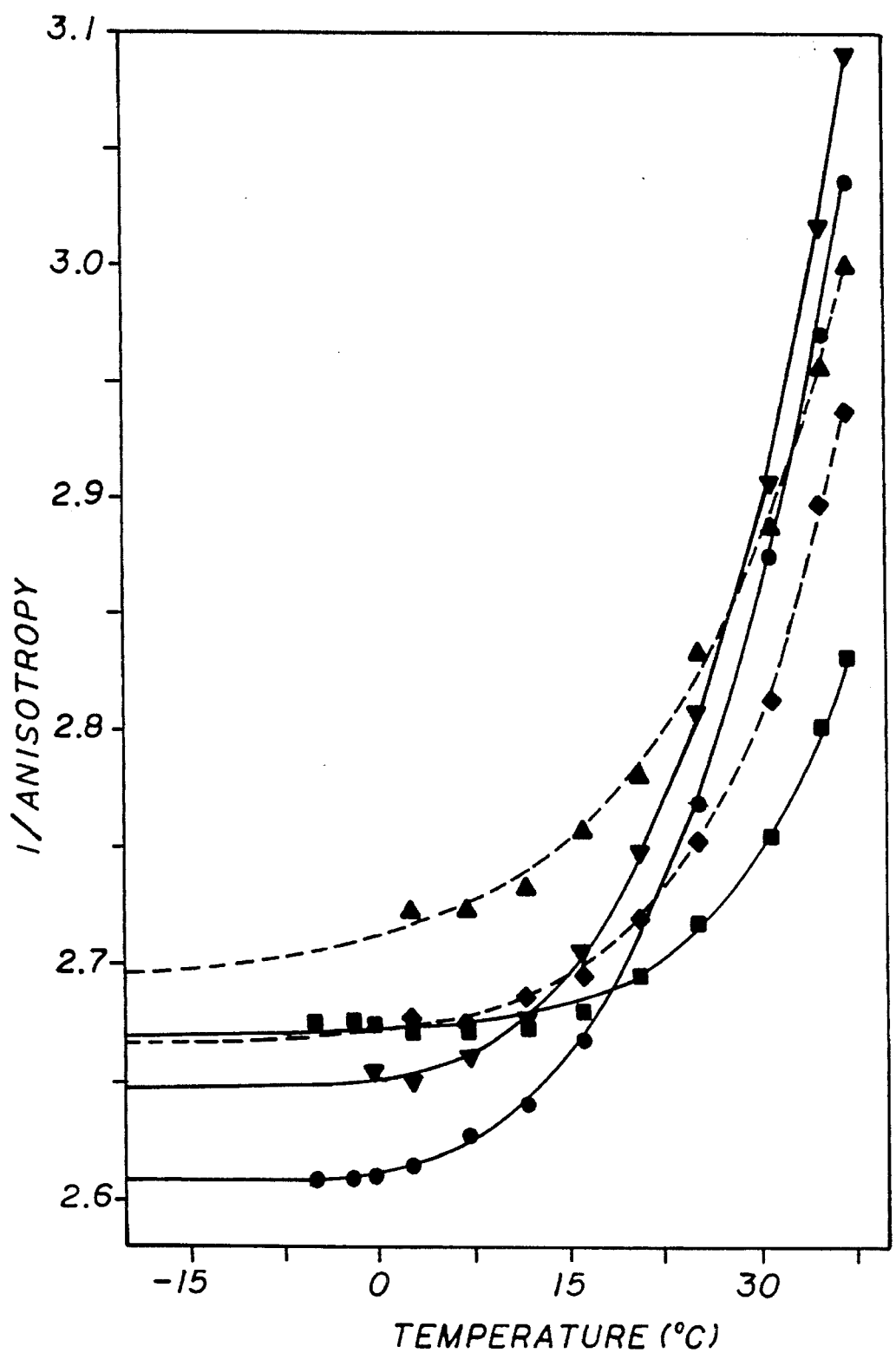
FIG. 5. is a plot of 1/anisotropy vs. temperature for camptothecin (circle), topotecan (triangle), 10,11-methylenedioxycamptothecin (square), 10-hydroxycamptothecin (diamond), and camptothecin carboxylate sodium salt (inverted triangle) in glycerol.

The limiting fluorescence anisotropy ($a_0$) values were also measured. The maximum values of (a) were obtained by dissolving the camptothecin drugs in the viscous solvent glycerol and cooling the samples to low temperatures. The steady state fluorescent values are shown in FIG. 5 and summarized in Table III. Steady-stated anisotropy (a) values were determined for samples containing 1 µM drug at 37° C.

Where the solvent viscosity is high and temperature is low, depolarizing rotations are at a minimum. By extrapolating these (a) values to −25° C., the limiting anisotropy values ($a_0$) for the camptothecin drugs, were determined. These values are summarized in Table III.

facil, from Pearce Chemical, Rockford, Ill. The titration was conducted at camptothecin drug concentration of $1 \times 10^{-6}$M in PBS at 37° C. Anisotropy values at each lipid concentration were determined within less than 30 seconds following the addition of the camptothecin drugs to the liposome suspension. The (a) values were determined for fixed drug concentration, typically 2 µM, while the lipid concentration was varied from 0 to 0.29M. By varying the lipid concentration rather than varying the drug concentration, the problem of self-association phenomenon which occurs for camptothecin drugs concentrations in excess of 10 µM is avoided. Also, the well-known phenomenon known as inner filter effect which occurs using fluorescent material at high optical densities is a is avoided.

Figure 4A:
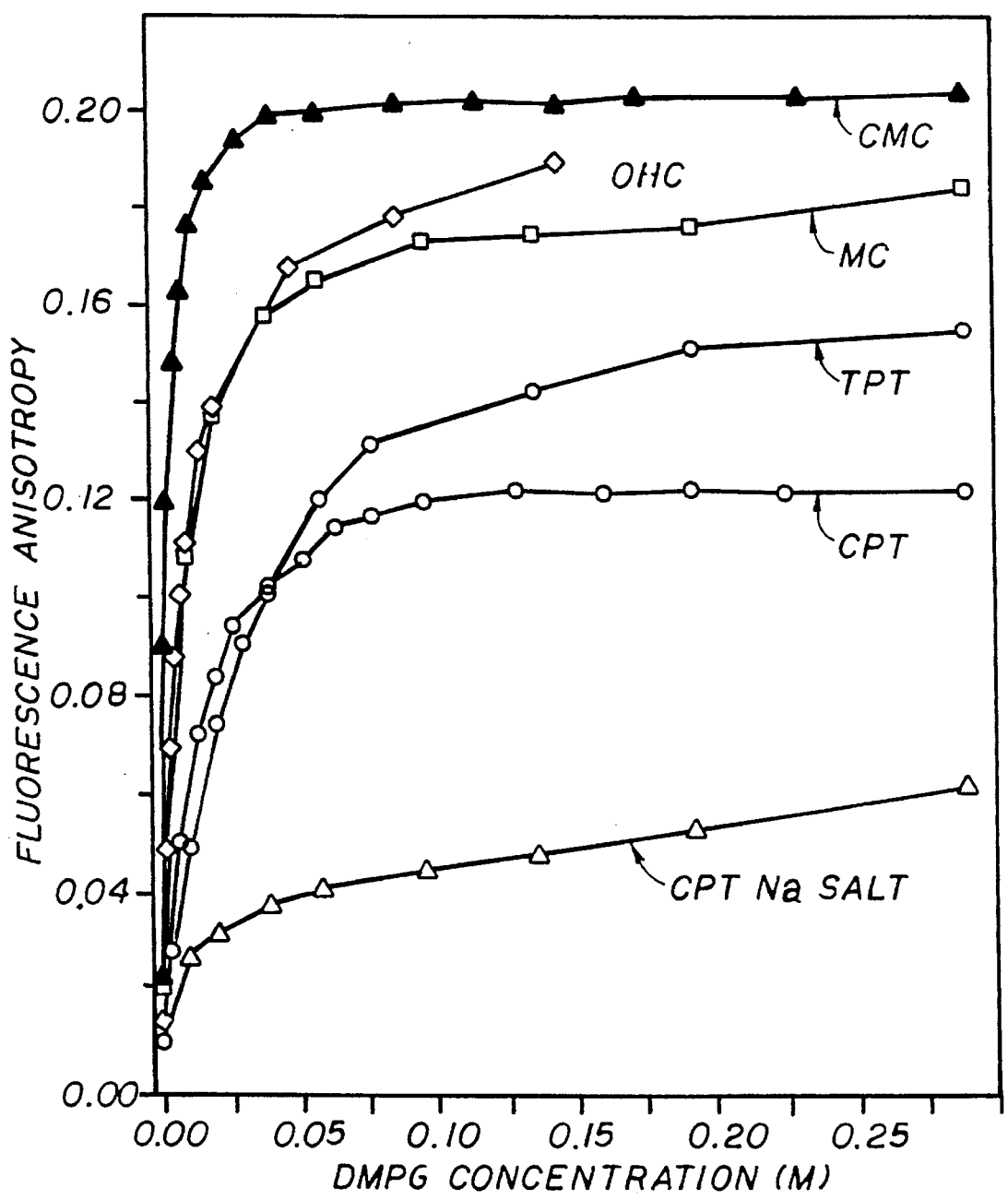
FIG. 4a. is an adsorption isotherm for CMC (solid triangle), 10-hydroxycamptothecin (open diamond), 10,11-methylenedioxycamptothecin (open square), topotecan (open circle), camptothecin (open circle), and camptothecin carboxylate sodium salt (open triangle) associated with DMPG liposomes.
Figure 4B:
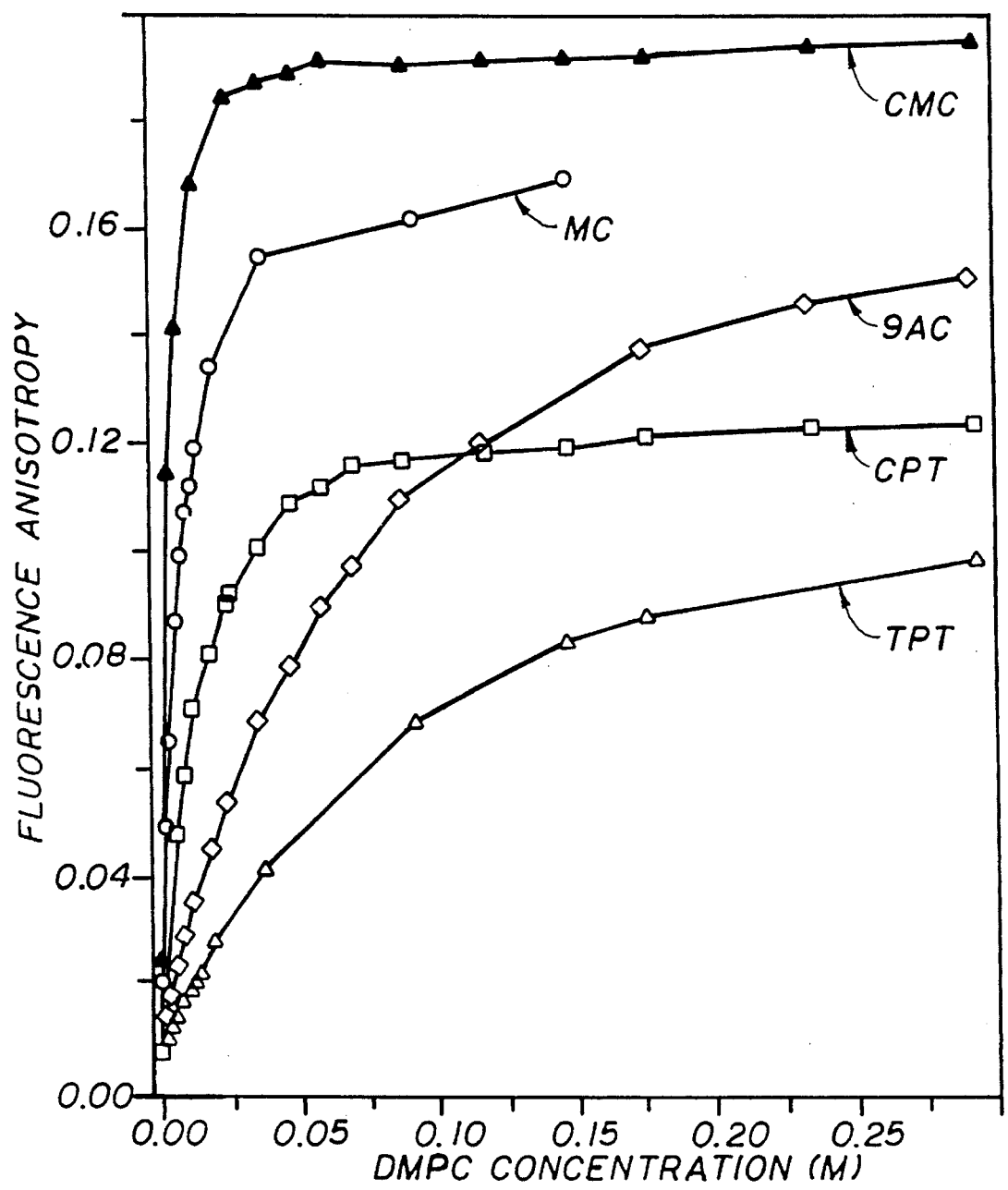
FIG. 4b. is an adsorption isotherm for 9-chloro-10,11-methylenedioxycamptothecin CMC (solid triangle), 10,11-methylenedioxycamptothecin (open circle), camptothecin (open square), and topotecan (open triangle), 9-aminocamptothecin (open diamond) associated with DMPC liposomes.

As a consequence of the brilliant fluorescence emission from camptothecin, camptothecin carboxylate sodium salt, 10-hydroxycamptothecin, topotecan, 10,11-methylenedioxycamptothecin, and 9-chloro-10,11-methylenedioxycamptothecin, the adsorption isotherms presented in FIGS. 4A and 4B are relatively free from any background signal. Drug from 0 to 0.29M. By varying the lipid concentration rather than varying the drug concentration, the problem of

TABLE III

Steady-state Anisotropy Values of Camptothecin Drugs in Various Solvents and in Liposomes Containing Different Phospholipid

| | Solvents at 37° C. | | | Membranes at 37° C. | | | |
| | | | | electro neutral | negatively charged | solid phase | |
| Drug | PBS | octanol | glycerol | DMPC | DMPG | DSPC | $a_0$ |
| --- | --- | --- | --- | --- | --- | --- | --- |
| camptothecin | 0.007 | 0.051 | 0.334 | 0.127 | 0.122 | 0.087 | 0.383 |
| camptothecin carboxylate[1] | 0.008 | 0.073 | 0.327 | 0.102 | | — | 0.377 |
| 10-hydroxy-camptothecin | 0.021 | 0.127 | 0.331 | 0.191 | 0.201 | — | 0.372 |
| topotecan | 0.008 | 0.071 | 0.320 | 0.125 | 0.170 | 0.059 | 0.367 |
| 10,11-methylenedioxy-camptothecin | 0.021 | 0.089 | 0.357 | 0.168 | 0.206 | — | 0.374 |
| 9-aminocamptothecin | 0.009 (pH 3) | — | — | 0.190 (pH 3) | — | — | — |
| 9-amino-10,11-methylene-dioxycamptothecin | 0.049 (pH 3) | — | — | 0.160 (pH 2) | — | — | — |
| 9-chloro-10,11-methylene-dioxycamptothecin | 0.025 | 0.098 | 0.363 | 0.202 | 0.207 | — | 0.367 |

— no data available
Steady-state anisotropy (a) values were determined on samples containing 1 µM drug at 37° C., and the a values have been corrected for background scatter (<1% in all cases). Camptothecin, camptothecin carboxylate sodium salt, and 10,11-methylenedioxycamptothecin were studies using $\lambda_{EX} = 370$ nm and 418 nm long wave pass filters on each emission channel. Topotecan samples were studied using $\lambda_{EX} = 390$ nm and 500 nm long wave pass filters on the emission channels.
Anisotropy values for liposome-bound drugs were determined by plotting 1/a vs. 1 [lipid].
[1]Camptothecin carboxylate sodium salt.

Typically, the fluorescent intensity level from camptothecin drugs in PBS buffer exceeded 99.98% (or 0.02% scatter), while the fluorescence signal from the liposomes having the highest lipid concentrations, 200 mg/ml, ranged from 99.5% to 99%. Because of the sensitivity of the value of (a) of the camptothecin drugs to association with the liposome membrane, fluorescence anisotropy titration was used to study the equilibrium binding of camptothecin drugs to liposomes.

The concentrations of free camptothecin drugs and camptothecin drugs associated with liposomes were determined at various lipid concentrations. All experiments were conducted in glass tubes pretreated with a silating agent, Surself-association phenomenon which occurs for camptothecin drugs concentrations in excess of 10 µM is avoided. Also, the well-known phenomenon known as inner filter effect which occurs using fluorescent material at high optical densities is a is avoided.

As a consequence of the brilliant fluorescence emission from camptothecin, camptothecin carboxylate sodium salt, 10-hydroxycamptothecin, topotecan, 10,11-methylenedioxycamptothecin, and 9-chloro-10,11-methylenedioxycamptothecin, the adsorption isotherms presented in FIGS. 4A and 4B are relatively free from any background signal. Drug concentrations of 2 µM and long pass filters to isolate emitted light from background signal (i.e. scattered exciting light and extraneous fluorescence signal due to the presence of impurities), were used. Signal levels from camptothecin drugs free in PBS solution were typically 99.97% and 99.3% in the presence of liposomes.

Adsorption isotherms like those shown in FIGS. 4A and 4B were used to determine overall association constants for the camptothecin drugs. Overall association constants are defined as:

$$K=[A_B]/[A_F][L] \quad \text{(Equation 2)}$$

where $[A_B]$ represents the concentration of the camptothecin drug bound to the vesicle membrane, $[A_F]$ represents the concentration of free drug, and $[L]$ represents the total lipid concentration in the liposome suspension. This equation is valid when the concentration of free lipid is approximately equal to the concentration of total lipid, that is, the concentration of free lipid is in great excess over the concentration of bound drug. Provided this concentration is satisfied, K may be determined from the inverse of the slope of a double reciprocal plot according to (Burke and Tritton, Biochemistry 24:1776, 1985). In such a plot, 1/bound fraction of the total camptothecin drug is plotted vs. 1/[lipid], with a y-intercept value of 1.

Figure 6:
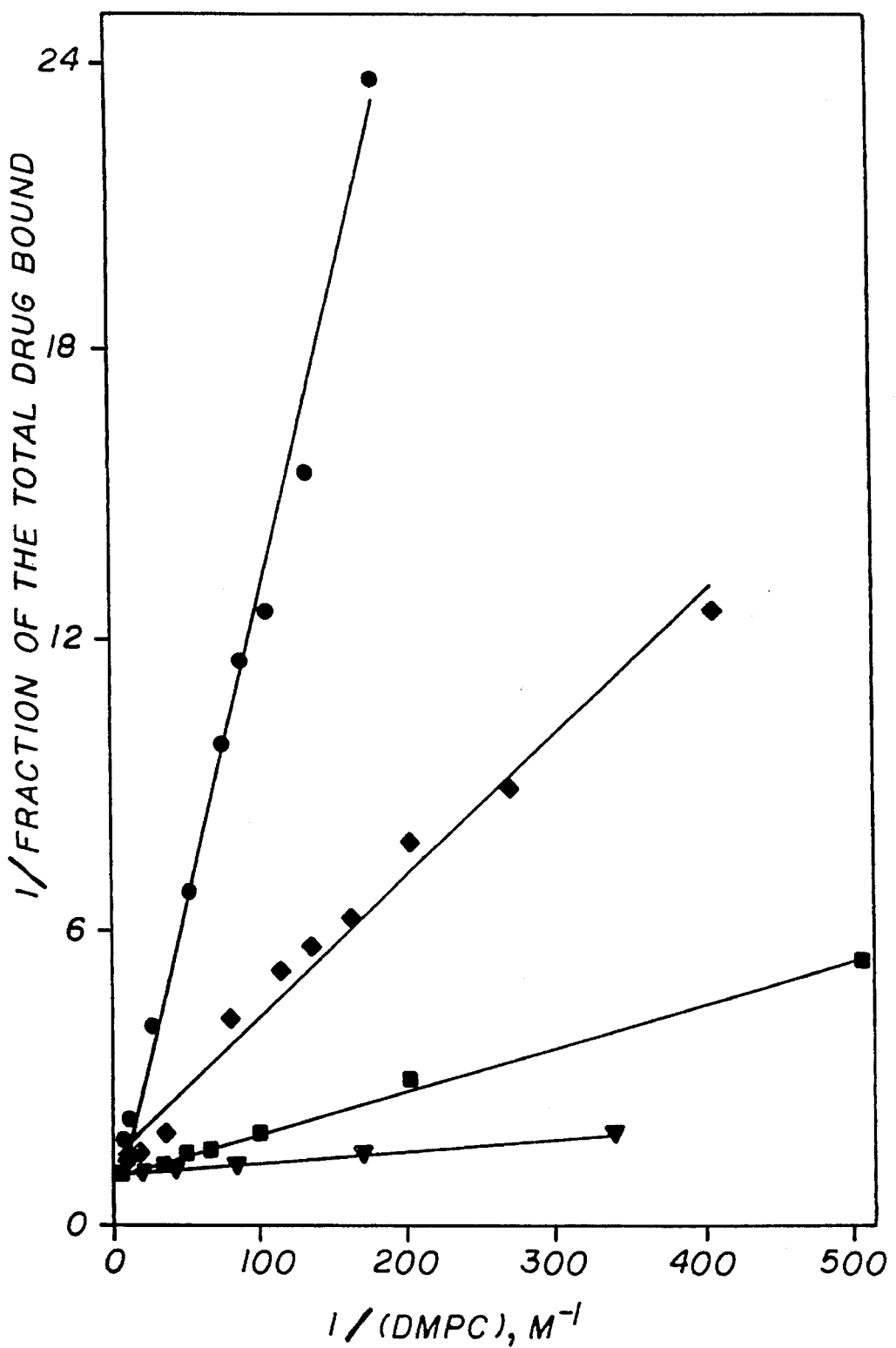
FIG. 6. is a double-reciprocal plot for the binding of CMC (inverted triangle), camptothecin (square), camptothecin carboxylate sodium salt (diamond), and topotecan (circle) to DMPC liposomes.

FIG. 6A is the double-reciprocal plot for the associations of CMC, camptothecin, camptothecin carboylate sodium salt and topotecan with DMPC at 37° C. The K values are summarized in Table IV. The linearity of these plots, as well as the corresponding plots for camptothecin drug associations with other types of liposome membranes, see FIGS. 6B and 6C, indicates that fluorophore binding at these lipid concentrations is adequately described by equation 2.

Camptothecin was found to bind both the DMPG and DMPC liposomes equally (K=100M$^{-1}$). At 0.29M lipid concentration, the maximum concentration studied, the camptothecin is essentially completely bound to the membrane of the liposome. As the lipid concentration is increased, the anisotropy value of the camptothecin increases, finally leveling off at the high lipid concentrations. At these high lipid concentrations where the slope of the plot has leveled off to close to zero, the camptothecin is essentially completely bound to the membrane of the liposome.

FIG. 4A shows a 17-fold enhancement in the steady-state anisotropy (a) value for camptothecin bound to DMPG liposomes. Similar results are shown in FIG. 4B for camptothecin bound to the electroneutral DMPC liposome. Camptothecin thus binds the two different types of liposome membranes equally well.

As seen in FIGS. 4A and 4B, the topotecan preferentially binds negatively charged DMPG liposomes as compared to DMPC liposomes.

The stabilization of camptothecin drugs was determined using different lipids. Three types of lipids (and thus 3 types of membranes) were examined: fluid-phase and electroneutral L-α-dimyristoylphosphatidylcholine (DMPC); fluid-phase and negatively-charged L-α-dimyristoylphosphatidylglycerol (DMPG), and solid-phase and electroneutral L-α-distearoylphosphatidylcholine (DSPC). While DMPC and DMPG have identical chain length, the charge on their head groups differ. DMPC and DSPC have identical head groups, but DMPC has acyl chains having 14 carbons per chain, which are four carbons shorter than the DSPC, which has 18 carbons per chain. This difference of 4-carbon chain length results in DMPC being fluid-phase at 37° C. while DSPC is solid-phase. The 7 camptothecin drugs listed in Table III were combined with liposomes containing the above lipids.

Of the camptothecin drugs examined, the 9-chloro-10,11-methylenedioxycamptothecin (CMC) has the highest liposome membrane affinities ($K_{DMPC}$=400M$^{-1}$; $K_{DMPG}$=320M$^{-1}$), followed by 10,11-methylenedioxycamptothecin and camptothecin, both of which have $K_{DMPC}$ and $K_{DMPG}$ values of 100M$^{-1}$ or greater. Hydrolysis of camptothecin to its carboxylate form resulted in a three-fold reduction in binding to the electroneutral DMPC liposomes. Topotecan, although positively-charged, has a $K_{DMPG}$=50M$^{-1}$ and thus, has a 6-fold reduced ability to bind negatively-charged liposome membranes relative to CMC. Topotecan which has a $K_{DMPC}$=10M$^{-1}$ has 40-fold reduced propensity to bind electroneutral liposome membranes relative to CMC.

Thus the only camptothecin drug which displayed a strong binding preference for the negatively-charged lipid DMPG was the positively-charged topotecan.

Both topotecan and camptothecin displayed binding preferences (5-fold and 3-fold, respectively) for solid-phase DSPC liposomes over fluid-phase DMPC liposomes. FIGS. 4A and 4B show the extent of camptothecin drug binding to liposomes as a function of lipid concentration for DMPC and DMPG liposomes. DMPC liposomes were made as in Example 1, at lipid concentrations from 0 to 0.29M, using CMC, 10-hydroxycamptothecin, 10,11-methylenedioxycamptothecin, topotecan, camptothecin, and camptothecin carboxylate sodium salt, as shown in FIG. 4B. DMPG liposomes were made as in Example 2, at lipid concentrations from 0 to 0.29M, using 9-chloro-10,11-methylenedioxycamptothecin CMC, 10,11-methylenedioxycamptothecin, camptothecin, and topotecan, 9-aminocamptothecin, as shown in FIG. 4A. The lipid concentration wasAnalysis of the data using double-reciprocal plots gave identical overall association/binding constants of 100M$^{-1}$. These constants are shown in Table IV.

TABLE IV

Overall Association Constants [K(M$^{-1}$)] for Camptothecin Drugs Associated with Liposomes

| Camptothecin Drug | MEMBRANE TYPE[1] | | |
|---|---|---|---|
| | electroneutral DMPC | negatively charged DMPG | electro neutral DSPC |
| camptothecin | 100 | 100 | 300 |
| 10-hydroxy-camptothecin | 75 | 75 | — |
| 9-aminocamptothecin | 25 (pH 3.0)[2] | | |
| camptothecin carboxylate[3] | 40 | — | — |
| topotecan | 10 | 50 | 50 |
| 10,11-methylenedioxy-camptothecin | 190 | 130 | — |
| 9-chloro-10,11-methylenedioxy-camptothecin | 400 | 320 | 500 |

[1] Both DMPC and DMPG are fluid-phase at 37° C., while DSPC is solid-phase at 37° C.
[2] The 9-aminocamptothecin drug was studied at solution pH = 3.0, where it is fluorescent
[3] Camptothecin carboxylate sodium salt As can be see from the data contained in Table IV, a strong modulation can be achieved through substitution at the 9 and 10 positions of ring A. For the seven compounds studied, the range in $K_{DMPC}$ values is 40-fold while a greater than 6-fold span is observed in the $K_{DMPG}$ values.

Thus, among the camptothecin drugs studied, the CMC has the highest binding affinity for each type of liposome, the 10,11-methylenedioxycamptothecin and camptothecin have intermediate binding affinities, while topotecan exhibits the lowest binding affinity for liposomes.

Liquid Chromatography

A high performance liquid chromatography assay was used to determine the rate of hydrolysis of camptothecin and topotecan free in aqueous solution and to compare such rates with the rate of hydrolysis for the same drugs when bound to the DMPG and DMPC liposome membranes. The assay was conducted under near physiological conditions; the pH was 7.4, the temperature was 37° C. and the ionic strength was physiological. A Spectroflow model 980 fluorescence detector coupled to an HP 3392A integrator which acquired and processed the chromatograms, was used. For camptoth- −20° C. for analysis at a later time, within 2 hours. Samples were monitored at time points from 0 minutes, that is, immediately following dissolution, up to 72 hours.

Figure 7A:
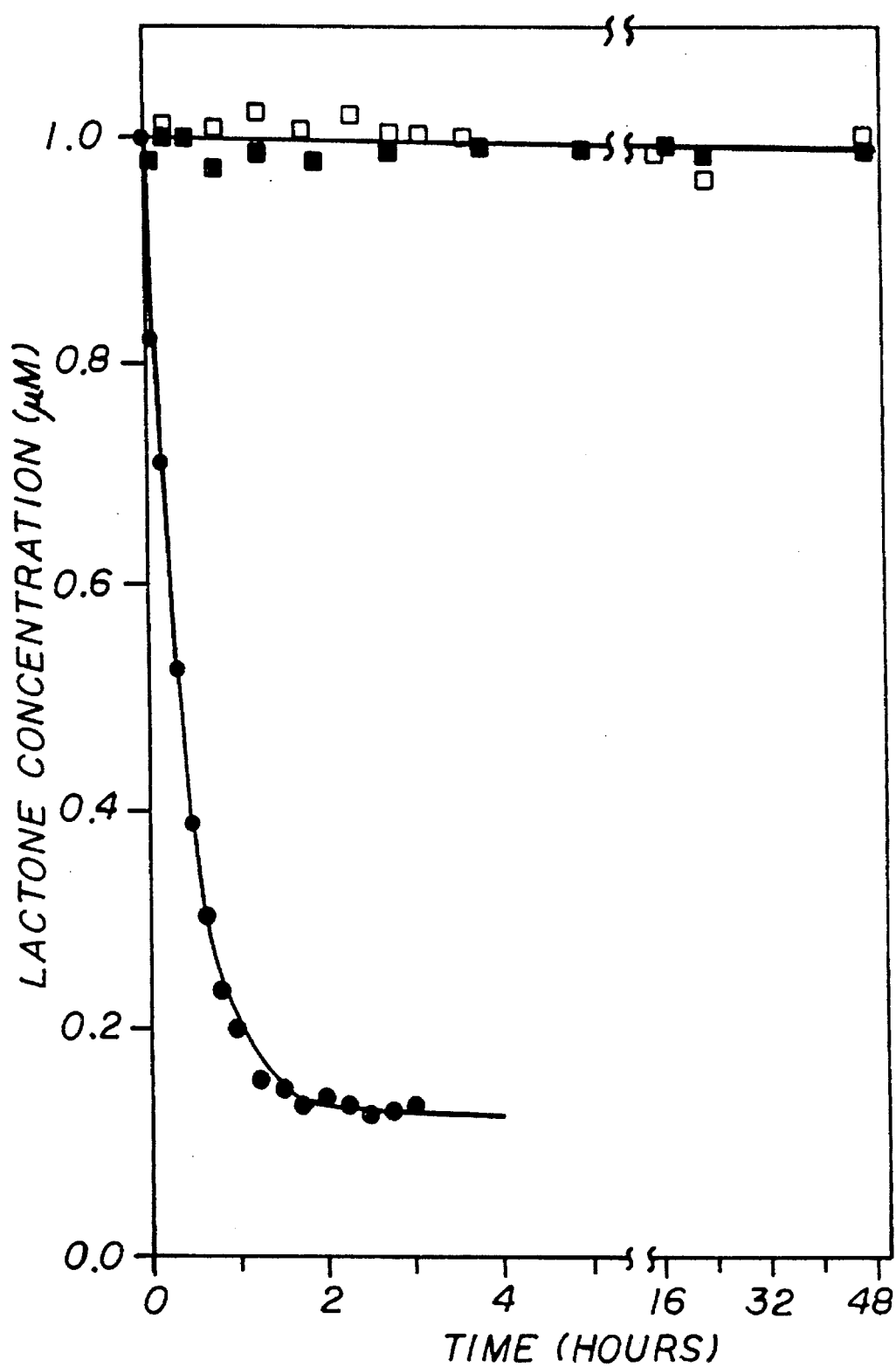
FIG. 7a. is a lactone concentration vs. time profile showing the rate of lactone ring hydrolysis for free camptothecin in PBS solution (circles), and for camptothecin drug associated with either DMPC liposomes (open squares) and DMPG liposomes (solid squares).
Figure 7B:
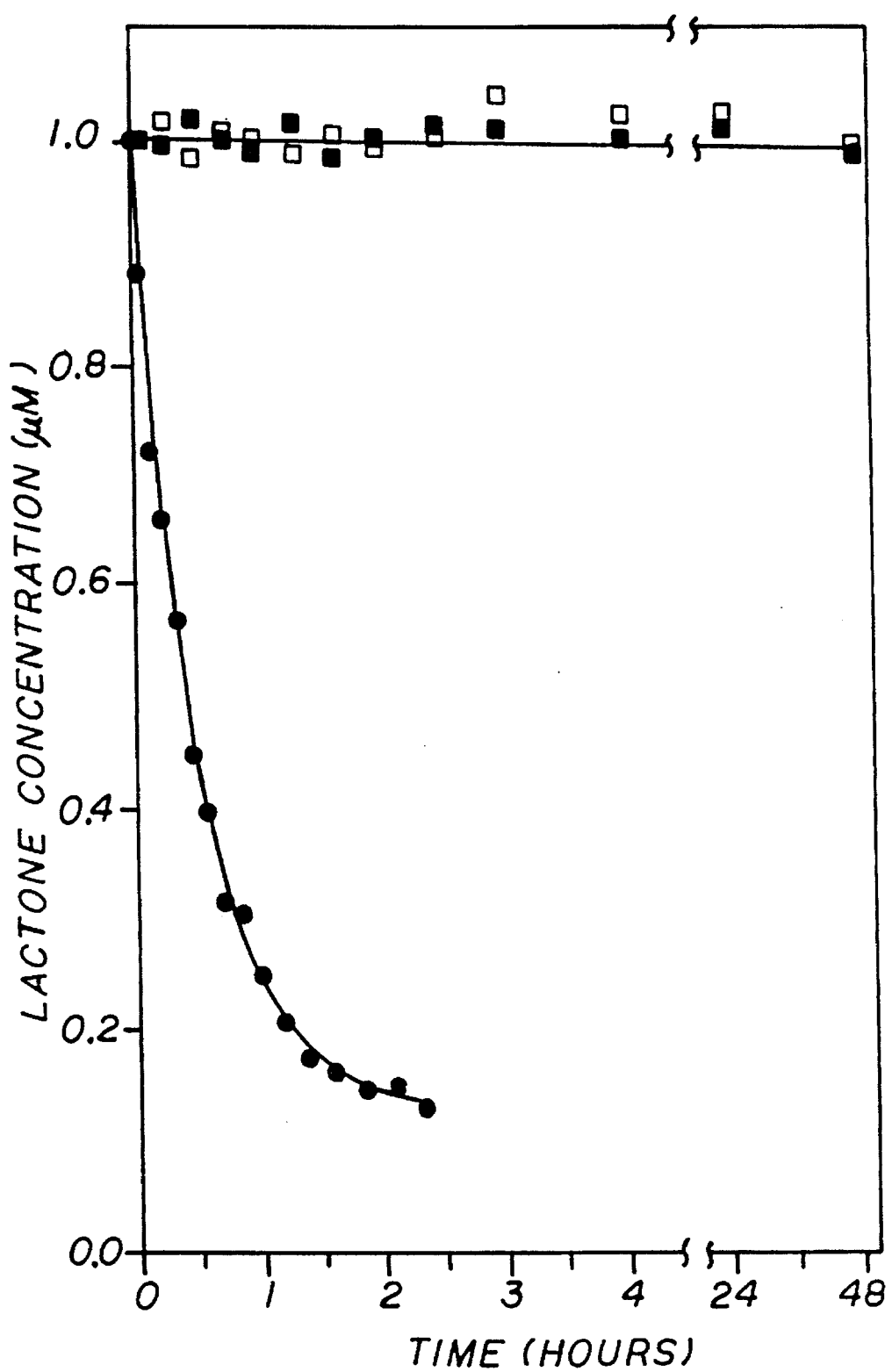
FIG. 7b. is a lactone concentration vs. time profile showing the rate of lactone ring hydrolysis for free CMC in PBS solution (circles), and for CMC drug associated with either DMPC liposomes (open squares) and DMPG liposomes (solid squares).
Figure 7C:
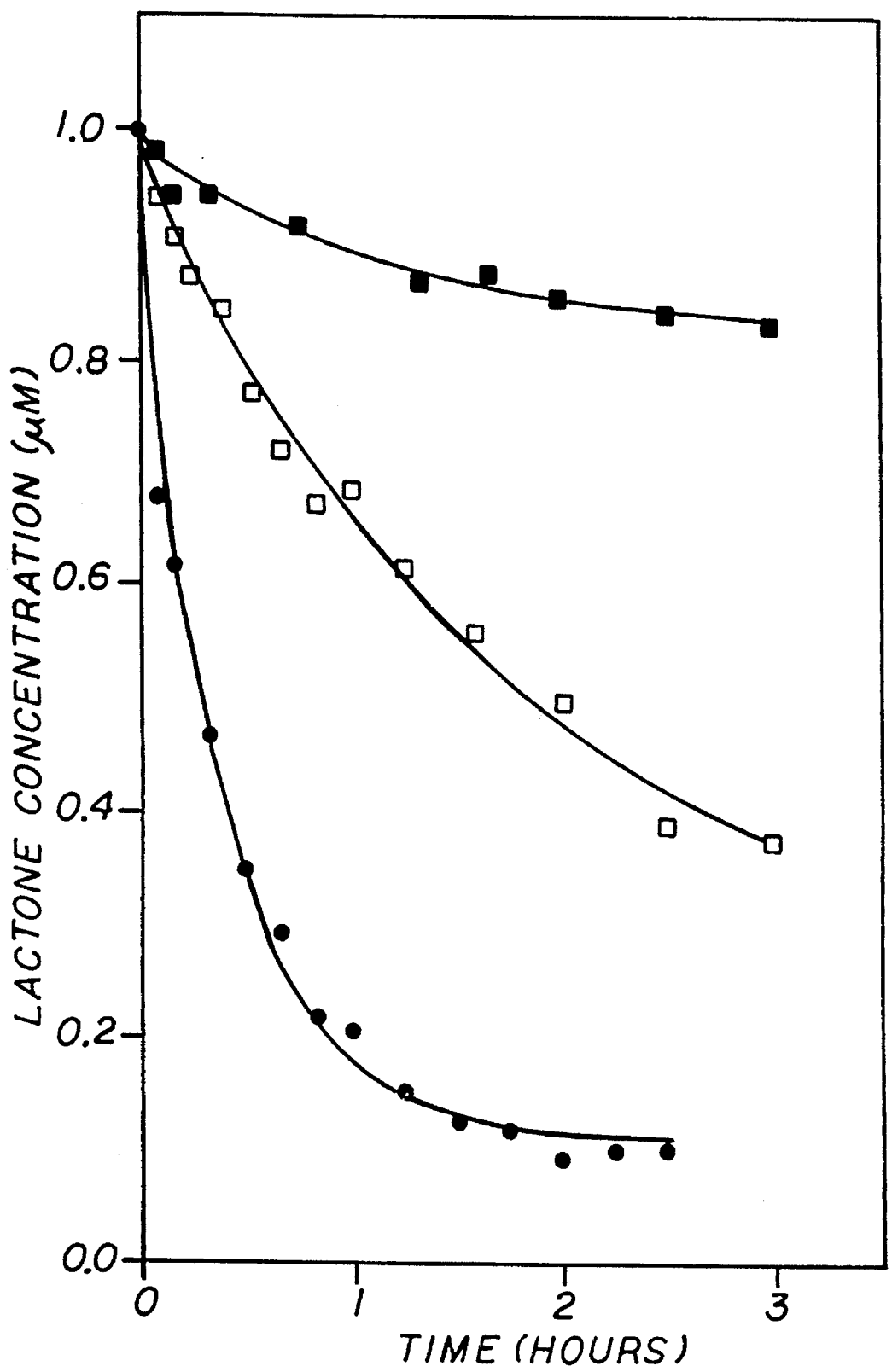
FIG. 7c. is a lactone concentration vs. time profile showing the rate of lactone ring hydrolysis for free topotecan in PBS solution (circles), and for topotecan drug associated with DMPC liposomes (open squares) and DMPG liposomes (solid squares).
Figure 7D:
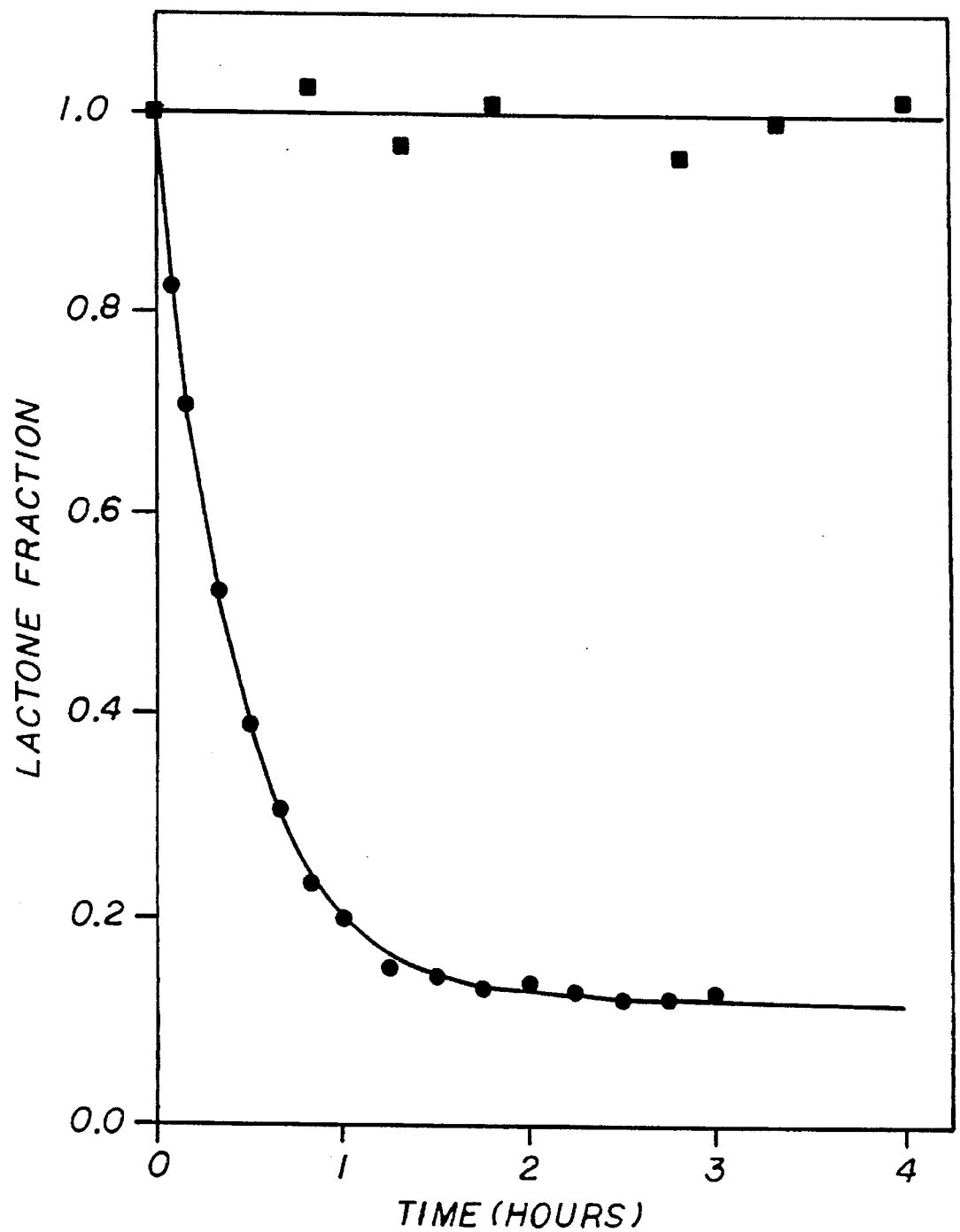
FIG. 7d. is a lactone concentration vs. time profile showing the rate of lactone ring hydrolysis for free 2 mM camptothecin in PBS solution (circles), and for 2 mM camptothecin associated with DMPC liposomes (squares).

The kinetics of lactone ring hydrolysis for free camptothecin, CMC and topotecan are shown in of FIGS. 7a, 7b and 7c. A stability profile for camptothecin at a reduced lipid:drug ratio of 150 is shown in FIG. 7D. Analysis of the decay profile for camptothecin, CMC and topotecan free in PBS was accomplished using a nonlinear least squares program. The stability data are presented in Table V.

TABLE V

Summary of the Kinetic and Equilibrium Parameters for the Hydrolysis of Camptothecin Drugs Free in PBS Buffer and Associated with DMPG, DMPC, and DSPC Liposomes.

| Drug | $t_{1/2}$ free drug | C/L free drug | $t_{1/2}$ drug DMPG Lip. | C/L drug DMPG Lip. | $t_{1/2}$ drug DMPC Lip. | C/L drug DMPC Lip. | $t_{1/2}$ drug DSPC Lip. | C/L drug DSPC Lip. |
|---|---|---|---|---|---|---|---|---|
| 9-aminocamptothecin | 22.5 | 6.0 | 49 min. | 0.15 | 56 min. | 0.45 | — | — |
| 9-amino-10,11-methylene dioxycamptothecin | 26.9 | 5.1 | — | — | — | — | — | — |
| camptothecin | 16.6 | 6.8 | >3 days | ~0 | >3 days | ~0 | ~100 min. | ~3.4 |
| 9-chloro-10,11-methylene dioxycamptothecin | 21.3 | 6.4 | >3 days | ~0 | >3 days | ~0 | — | — |
| 10-hydroxycamptothecin | 23.9 | 5.4 | — | — | — | — | — | — |
| 10,11-methylene-dioxycamptothecin | 28.7 | 3.3 | >3 days | ~0 | >3 days | ~0 | — | — |
| topotecan | 21.1 | 7.5 | 96 min. | 0.42 | 74.9 min. | 3.4 | — | — |
| 9-nitrocamptothecin | 23.8 | 7.5 | — | — | — | — | — | — |

$t_{1/2}$ = $t_{1/2}$ value (min$^{-1}$)
C/L - carboxylate/lactone ratio ecin, an Ultrasphere ODS C-18 250 mm long column was used. The mobile phase consisted of 32% acetonitrile, 67% 0.1M acetate buffer, pH 5.5, and 1% 01.M sodium dodecylsulfate at a flow rate of 1 mL/min. The detector was set to 370 nm excitation wavelength and a 418 nm long pass emission filter. A 1 μM solution of camptothecin in PBS was prepared and incubated at 37° C. Immediately after mixing the drug stock solution with PBS and at intervals of 5 min thereafter, 50 μL aliquots were taken out and mixed with 150 μL methanolic internal standard, 9-toluoylamidocamptothecin and either analyzed immediately or kept cold under dry ice. 150 μL of this mixture was diluted with 125 μL water and 200 μL was injected. The ratio of the peak areas corresponding to the intact lactone form of the camptothecin drug and the internal standard at a particular time was normalized to that at the time of mixing and was considered as the concentration of the intact lactone form.

For topotecan the excitation wavelength was 362 nm and the emission was observed through a 470 long wave pass filter. The stationary phase was Waters Nova-Pak C-18 150mm long column. The mobile phase consisted of 500 mL 0.1M KH$_2$PO$_4$, 550 mL acetonitrile, 4.2 mL triethylamine (distilled over molecular sieves), 4.44 g sodium dioctylsulfosuccinate (DOSS), and 970 ml water. The pH was adjusted to 6.0 with H$_3$PO$_4$. Internal standard solution contained 50×10$^{-9}$ g acridine from Eastman and 20×10$^{-3}$M DOSS in methanol and was always kept cold at ≦−20° C. Next 150 μL or cold internal standard solution was mixed with 50 μL aliquot containing topotecan, centrifuged for 1 minute and the supernatant was either analyzed immediately or stored at The data in Table V indicate that free camptothecin is very unstable in aqueous PBS solution, rapidly converting to the inactive carboxylate form of the drug with a half-life ($t_{1/2}$ value) of 16.6 min. A final equilibrium is reached where the inactive carboxylate form predominates in great excess the carboxylate:lactone ratio being 6.8:1. The other camptothecin drugs are also hydrolyzed quickly.

Similarly, the hydrolysis of the other free camptothecin drugs proceeds rapidly. The $t_{1/2}$ value for topotecan in PBS was 21.2 min., with a final equilibrium carboxylate:lactone ratio of 7.5. While the $t_{1/2}$ values range from 16.6 minutes for camptothecin, to 28.7 minutes for the 10,11-methylenedioxycamptothecin, the final equilibrium carboxylate:lactone ratios range from 5.1 to 7.5.

However, the data for the camptothecin drugs bound to the liposomes indicates that the lactone ring is protected from hydrolysis when associated with DMPC or DMPG liposomes. Even after 48 hours, more than 97% of the biologically active form of camptothecin, 9-chloro-10,11-methylenedioxycamptothecin and 10,11-methylenedioxycamptothecin are present. The data indicates that the camptothecin drug is soluble in phospholipid bilayer membranes, and that the camptothecin drugs are thus protected from hydrolysis.

No physical correlation is apparent between the relative hydrophobicities of the camptothecin drugs and their half-lifes. For example, CMC is the most lipophilic of the drug in Table V while topotecan is the least lipophilic, but both drugs display similar $t_{1/2}$ values of approximately 21 minutes.

FIGS. 7A, 7B and 7C also show the stability profiles of CMC, camptothecin, and topotecan in the presence of DMPC and DMPG liposomes having lipid concentrations of 0.29M. In samples containing DMPC liposomes, the bound drug levels for CMC, camptothecin, and topotecan were estimated 99%, 97%, and 74% respectively; while bound drug levels in samples containing DMPG liposomes were 99%, 97%, and 93%, respectively.

CMC and camptothecin when bound to liposomes, are stable for at least 48 hours. However, samples containing the less lipophilic drug topotecan showed some hydrolysis at 1 hour even when associated with liposomes. Based upon the $K_{DMPC}$ and $K_{DMPG}$ values for topotecan of $10M^{-1}$ and $50M^{-1}$, respectively, the bound topotecan levels of were estimated to be 74% for DMPC liposomes and 93% for DMPG liposomes. Consistent with these estimates, as shown in FIG. 7c, the topotecan is stabilized to a greater degree in DMPG liposomes as compared to DMPC liposomes. The lipophilic 10,11-methylenedioxycamptothecin was found to be stable when combined with either DMPC liposomes or DMPG liposomes with little hydrolysis even at 48 hours. The liposome membrane also stabilized the lactone rings of 9-aminocamptothecin and 9-amino-10,11-methylenedioxycamptothecin; although, since these drugs are less lipophilic, some hydrolysis occurred at 1 hour even when associated with liposomes. The lactone ring hydrolysis did not exceed 40% for either 9-aminocamptothecin or 9-amino-10,11-methylenedioxycamptothecin at time points of 5 hours in either the DMPG or DMPC liposomes.

To assess the effect of increased drug levels on the stability of camptothecin, MLVs prepared as in Example 5 and SUVs prepared as in Example 1 were made containing the same 0.29M DMPC concentration, but the camptothecin concentration was raised to 2 mM. Despite the 1000-fold increase in camptothecin concentration, the bound camptothecin levels remained at 97% since the at a concentration of 0.29M, the DMPC is still present in great excess and dominates the binding equilibrium. At the higher drug concentrations, where the lipid to drug ratios are 150, no evidence of lactone ring hydrolysis was observed, see FIG. 7D.

Iodide Quenching

Additional evidence that the fluorochrome of the camptothecin drugs penetrates into the membrane of the liposome comes from iodide quenching data. Iodide has an immeasurably small permeation of the liposome membrane and is able to discriminate between camptothecin drug molecules free in solution and those molecules located in the interior of the liposome membrane. These methods have been described in detail in Burke and Tritton, *Biochemistry* (1985) 24: 5972–5980; G. L. Jendrasiak, *Chem. Phys. Lipids* 9: 133–146 (1992); and, M. Cranney et al. *Biochem. Biophys. ACTA* 735, 418–425, which are incorporated herein by reference. The quenching studies were conducted using 0.5M iodide in PBS buffer.

The quenching of fluorescence of both camptothecin free in PBS and liposome membrane bound camptothecin by iodide ions was conducted at a constant halide concentration of 0.5M, in the presence of 2 mM sodium thiosulfate to prevent the oxidation of iodide. The camptothecin concentration was $1\times10^{-6}M$ and the iodide concentration was varied from 0 to 0.5M, and the chloride concentration was adjusted accordingly. The quenching experiments for the camptothecin bound to DMPC or DMPG liposome membranes were done at a lipid concentration of 100 mg/mL, so that the fraction of the bound camptothecin was more than 97%.

Figure 8:
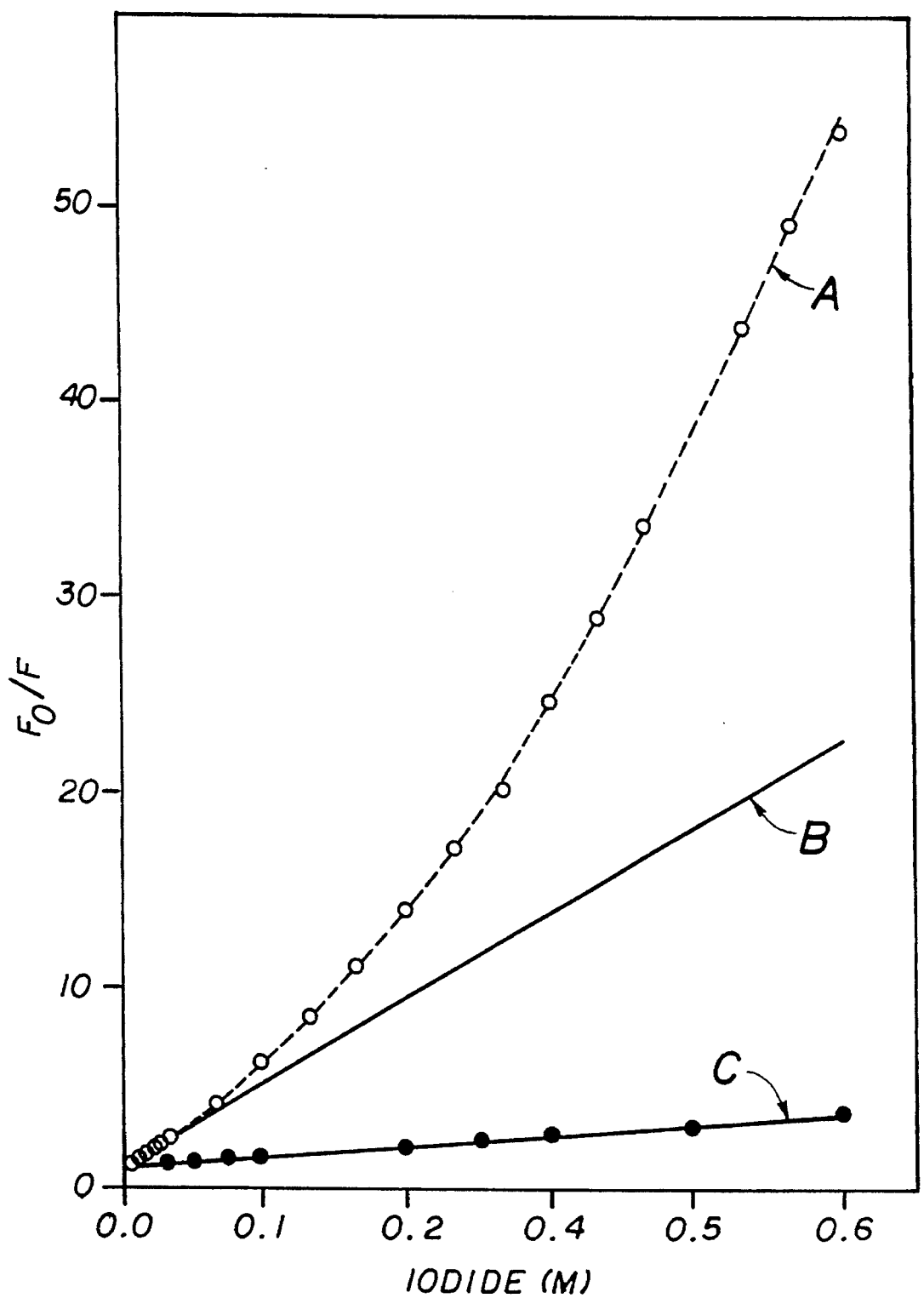
FIG. 8. shows iodide quenching of camptothecin free in solution (open circles), and bound to DMPC liposomes (solid circles).

Results of the iodide quenching experiments are shown in FIG. 8. Fluorescence of camptothecin free in PBS having a pH of 7.4 is quenched significantly by 0.5M iodide, $F_0/F$ being about 54.3. Fluorescence of the liposome membrane bound camptothecin is quenched to relatively lower extent, for instance, $F_0/F$, for camptothecin bound to DMPC liposomes is only 4.1 (see Plot C). Also, there is a clear cut upward curvature in the $F_0/F$ vs. [I] plot (curve "A", FIG. 5) for camptothecin free in PBS whereas $F_0/F$ vs. [I] plot for camptothecin bound with DMPC membranes is linear. Quenching of fluorescence is believed to proceed via the dynamic (or collisional) and static quenching processes. Fluorescence quenching by a quencher molecule in contact with the fluorophore at the instant of excitation is considered to be static quenching. The static and dynamic quenching processes are separated by the following modified form of the Stern-Volmer equation (Eftink & Ghiron, 1976):

$$F_0/Fe^{v[Q]}=1+K_{sv}[Q] \quad \text{(Equation 3)}$$

where, V is the static quenching constant and $K_{sv}$ the dynamic or collisional quenching constant. The V and $K_{sv}$ values were obtained by fitting the quenching data to equation 3 with a value of V which gave the best correlation coefficient for the plot of $F_0/Fe^{v[Q]}$ vs. [Q]. The upward curvature of the quenching data of free camptothecin free in PBS seen in FIG. 8 could be attributed to the static quenching process. The straight line "B", which is tangential to the $F_0/F$ vs. [I] plot for free camptothecin in PBS, represents the dynamic part of the iodide quenching of camptothecin fluorescence, the slope of which is equal to $K_{sv}$ (slope=44 $3M^{-1}$ where $V=14M^{-1}$ correlation coefficient=0.9993). The Stern-Volmer plot for the liposome bound camptothecin is linear, curve "C", FIG. 8, the slope being $6.1M^{-1}$. It is evident that DMPC liposome bound camptothecin does not involve any significant static quenching process, probably due to the location of the fluorophore well inside the liposome membrane. The dashed line represents the static and dynamic quenching components camptothecin free in solution is determined by $F_0/F$ values.

While camptothecin free in solution was quenched readily by iodide ($V=1.8M^{-1}$; $K_{sv}=44.3M^{-1}$), camptothecin bound to DMPC liposomes was much more difficult to quench ($V=0M^{-1}$; $K_{sv}=6.2M^{-1}$). The camptothecin associated with the liposomes is thus much less accessible to quenching by iodide, indicating that the fluorochrome of the drug is located deep with the phospholipid bilayer membrane.

The picosecond fluorescence experiment were carried out with a Piridine I cavity dumped dye laser and frequency doubled light 365 mm. The lifetime and correlation time were measured using frequency domain fluorometer operating up 10 GHz (Laczko et al., *Rev. Sci. Instrum.* 61: 2331, (1990)). The modulated exited light was obtained from the harmonic content of a laser pulse train with a repetition rate of 3.81 MHz and a pulse width of 5 ps. A mode locked Ne:Yag Antares laser was used to pump the dye laser. The emission was observed through the cut of the filter 420 mm by microchannel photomultiplier. The cross-correlation detection was done outside the photomultiplier tube, according to Laczko et al., *Rev, Sci. Instrum.* 61: 2331 (1990).

Figure 9:
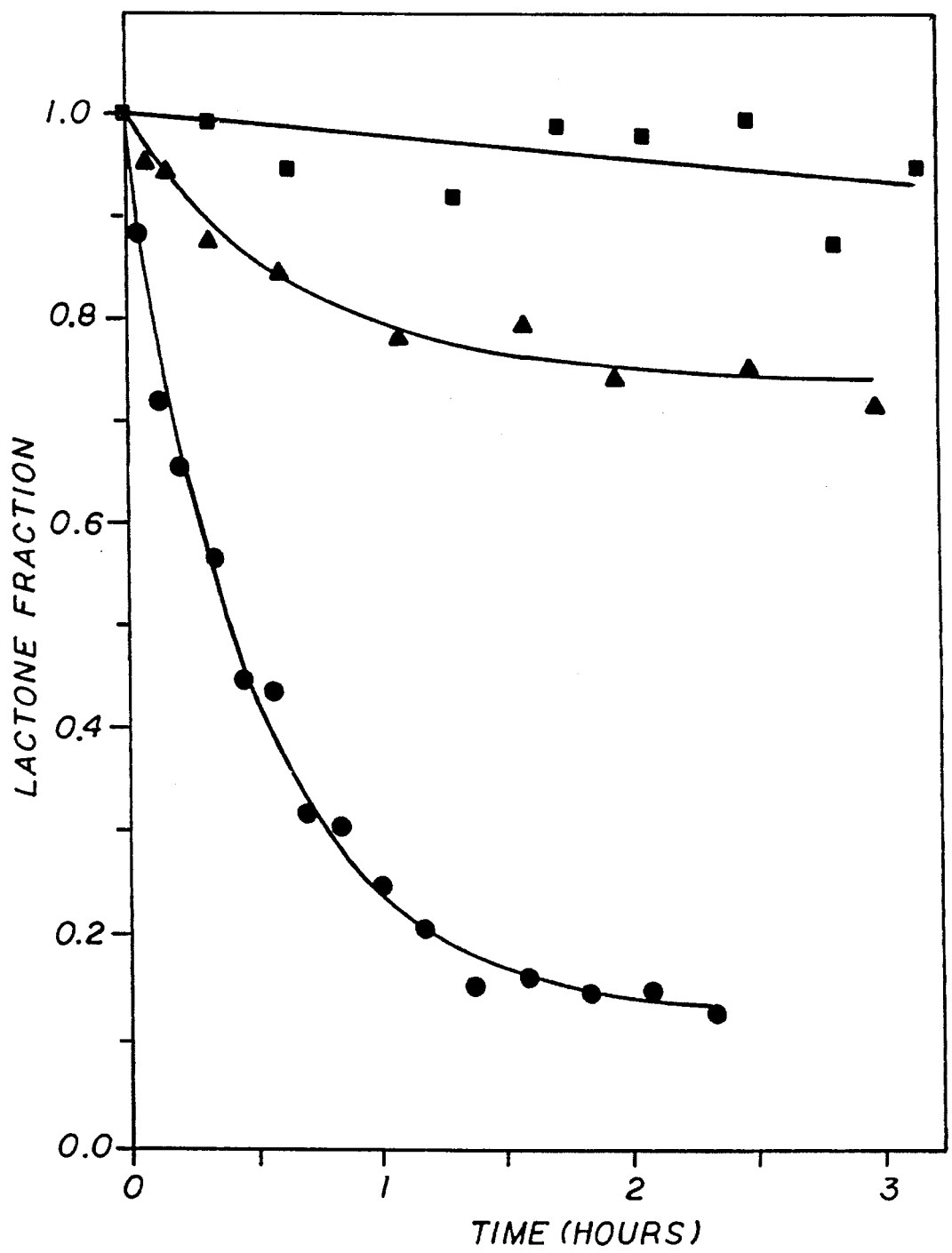
FIG. 9. is a lactone concentration vs. time profile showing the rate of lactone ring hydrolysis for free 9-chloro-10,11-methylenedioxycamptothecin in PBS at a pH of 7.4 (circles) and 9-chloro-10,11-methylenedioxycamptothecin associated with DSPC MLVs at a pH of 5.0 (square). The triangles represent data showing that liposome lysis by sonication (5 minutes) releases 9-chloro-10,11-methylenedioxycamptothecin which is then hydrolysed.

The lactone rings of camptothecin drugs are stable at low pH, that is below pH 6. Accordingly, CMC DSPC liposomes (MLVs) were prepared according to example 7, to provide an internal pH of 5. As can be seen in FIG. 9, the CMC is stabilized in the liposomes having a pH of 5 (squares) as compared to free CMC(circles). More than 80% of the lactone ring is not hydrolysed. The CMC is stabilized despite the reduction in total lipid concentration. Also, the CMC is stabilized in such liposomes, whether the external pH is at 7.4 or 5. When such CMC DSPC liposomes are partially lysed by sonication for 5 minutes, the CMC is at least partially released and hydrolysed.

Thus for camptothecin drugs which have a low binding affinity or even an intermediate binding affinity for liposome or micelle membranes, such as CMC, camptothecin, topotecan, and 9-aminocamptothecin, these drugs can be further stabilized by lowering the pH of the compartment of the liposome or micelle.

The fact that liposome-associated camptothecin drugs are stable indicate that the lactone ring of the camptothecin drugs penetrates into the liposome membrane. The 10,11-methylenedioxycamptothecin, and 9-chloro-10,11-methylenedioxycamptothecin are preferred for use with liposomes of because of their lipophilicity and thus improved binding to lipid membranes. It is preferred that the 10,11-methylenedioxycamptothecin, and 9-chloro-10,11-methylenedioxycamptothecin be associated with either DMPG liposomes, or DSPC liposomes having a pH of less than 6. Generally, the DMPG is preferred over the DMPC. Thus camptothecin drugs are stabilized in liposomes either by binding the liposome membrane or by locating in the compartment where the pH is lower than 6, preferably 5 or below.

Characterization of Camptothecin Drugs Associated with Micelles.

Figure 10:
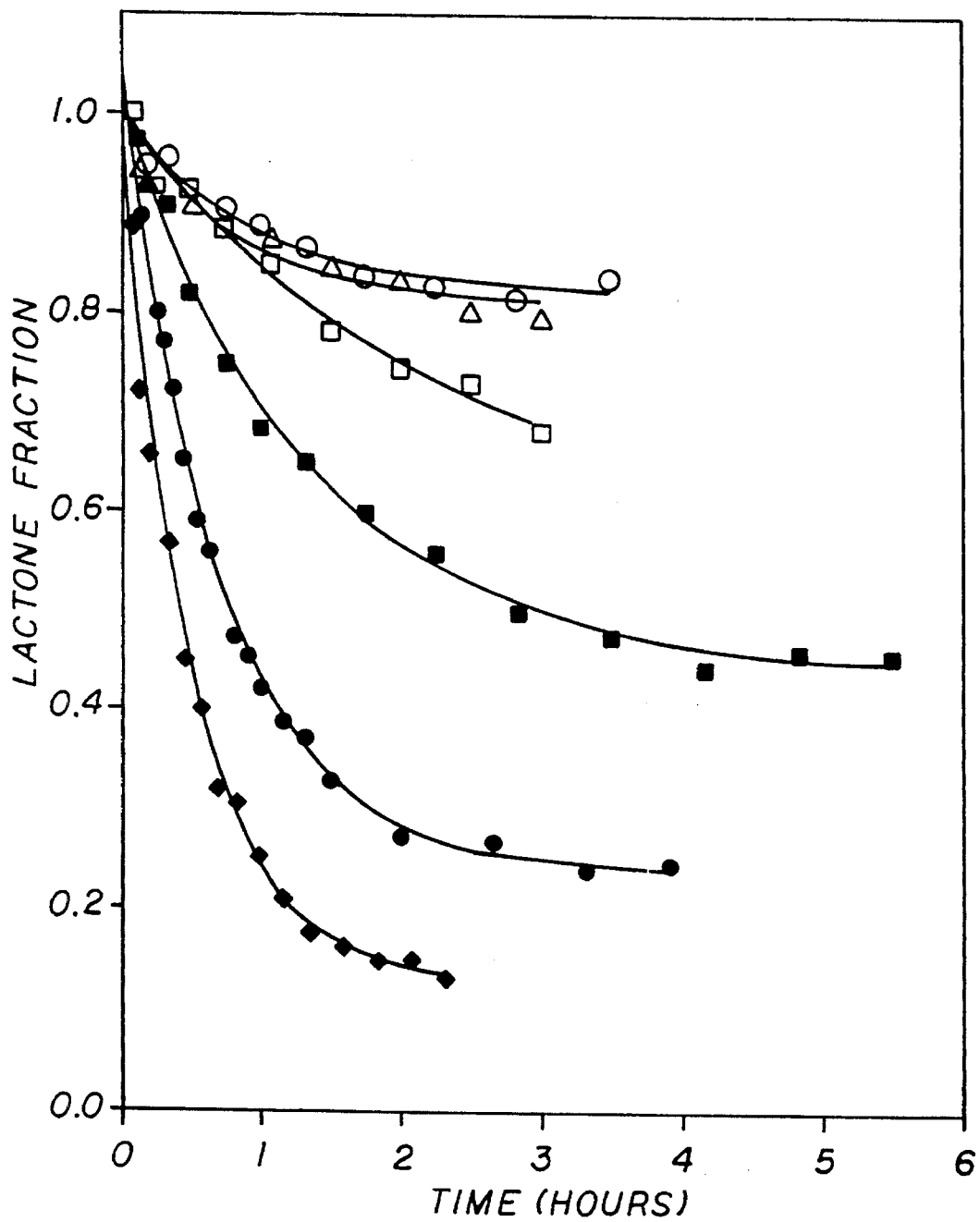
FIG. 10. is a lactone concentration vs. time profile showing the rate of lactone ring hydrolysis for 10,11-methylenedioxycamptothecin: free in PBS solution at pH 7.4 (closed circles); associated with micelles composed of SDS (open triangles); associated with micelles composed of sorbitan mono-oleate (closed squares); and associated with micelles composed of octylphenolpolyethyleneglycol (open squares). Also shown is the rate of lactone ring hydrolysis for CMC free in PBS (closed diamonds) and associated with micelles composed of sorbitan mono-oleate (200 mg/ml) (open circles).

FIG. 10 shows the rate of hydrolysis for 10,11-methylenedioxycamptothecin free in PBS solution; in less than 1 hour, more than 70% of the drug is hydrolyzed. However, as FIG. 10 also shows, when the 10,11-methylenedioxycamptothecin is associated with sorbitan mono-oleate micelles; the $t_{1/2}$ is 55 minutes and 50% of the drug is stabilized even at 5 hours. The 10,11-methylenedioxycamptothecin is also stabilized by the SDS micelles; the $t_{1/2}$ is 39 minutes and at about 2.5 hours about 75% of the drug is not hydrolysed. Similarly the drug is stabilized by the octylphenolpolyoxyethylene; the $t_{1/2}$ is 90 minutes.

Figure 11:
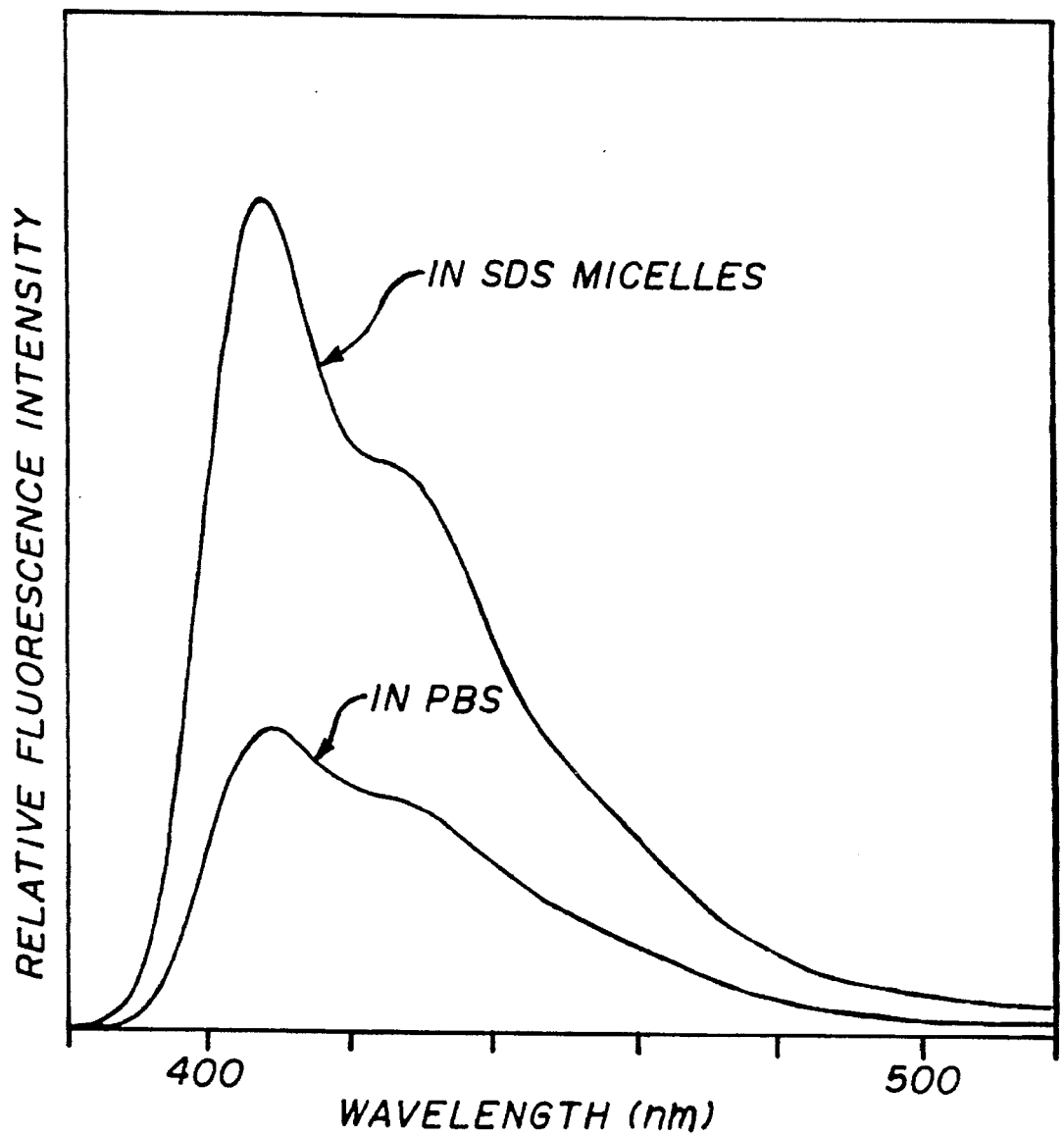
FIG. 11. is the fluorescence emission spectra of free 10,11-methylenedioxycamptothecin in PBS solution and for 10,11-methylenedioxycamptothecin associated with micelles composed of the surfactant sodium dodecylsulfate (SDS).

FIG. 11, an excitation and emission spectra for 10,11-methylenedioxycamptothecin, shows that where the drug associated with SDS micelles the lactone ring is protected from hydrolysis. For the CMC, it is preferred that the sorbitan mono-oleate surfactant be used; for the 10,11-methylenedioxycamptothecin, it is preferred that the SDS be used.

Liposomes are preferred over micelles composed of entirely of surfactants, that is, lacking lipid, because the camptothecin drugs are more stable in the liposomes and because liposomes are composed of lipids which occur naturally in the patient's body.

Thus liposomes and micelles composed of camptothecin drugs are an effective means of conserving the intact, active forms of the drugs; clinical use of such liposomes and micelles will aid in controlling the proliferation of tumorous tissue in patients undergoing chemotherapy.

I claim:

1. A liposome, comprising a camptothecin drug or mixtures of camptothecin drugs containing a least one lactone ring, and a bilayer membrane comprised of lipid, at least some of the said lactone ring being intercalated in the bilayer so that said ring is protected from hydrolysis at an internal liposomal compartment pH of from about 3 to about 7.4.

2. The liposome of claim 1, wherein the drug comprises 10-hydroxycamptothecin.

3. The liposome of claim 1, wherein the drug comprises topotecan.

4. The liposome of claim 1, wherein the drug comprises 9-aminocamptothecin.

5. The liposome of claim 1, wherein the drug comprises 9-nitrocamptothecin.

6. The liposome of claim 1, wherein the drug comprises 10,11-methylenedioxycamptothecin.

7. The liposome of claim 1, wherein the drug comprises 9-amino-10, 11-methylenedioxycamptothecin.

8. The liposome of claim 1, wherein the drug comprises 9-chloro- 10,11 -methylenedioxycamptothecin.

9. The liposome of claim 1, wherein the drug comprises camptothecin.

10. The liposome of claim 1, wherein the lactone ring is contained in the compartment; wherein the pH of a compartment is from about 3 to about 6.

11. The liposome of claim 1, wherein the lipid is selected from the group consisting of: phosphatidylcholine; phosphatidylglycerol; and mixtures thereof; and the drug is selected from the group consisting of: camptothecin; 10-hydroxycamptothecin; topotecan; 9-aminocamptothecin; 9-nitrocamptothecin; 10,11-methylenedioxycamptothecin; 9-amino-10,11-methylenedioxycamptothecin; 9-chloro-10,11-methylenedioxycamptothecin; and mixtures thereof.

12. The invention of claim 1, wherein the lipid is dimyristoylphosphatidylcholine.

13. The invention of claim 1, wherein the lipid is distearoylphosphatidylcholine.

14. The invention of claim 1, wherein the lipid is dimyristoylphosphatidylglycerol.

15. The liposome of claim 1, wherein the liposome is unilamellar.

16. The liposome of claim 1, wherein the liposome is multilamellar.

17. A method for delivering camptothecin drugs to a host, comprising the steps of:

1. providing a liposome as a delivery vehicle comprising: a camptothecin drug or mixtures of camptothecin drugs containing a least one lactone ring, and a bilayer membrane comprised of lipid, at least some of the said lactone ring being intercalated in the bilayer so that said ring is protected from hydrolysis at an internal liposomal compartment pH of from about 3 to about 7.4;

2. administering the liposome to the host.

* * * * *